(12) United States Patent
Furukawa et al.

(10) Patent No.: US 11,873,269 B2
(45) Date of Patent: Jan. 16, 2024

(54) METHANOL PRODUCTION SYSTEM AND METHANOL PRODUCTION METHOD

(71) Applicant: MITSUBISHI HEAVY INDUSTRIES, LTD., Tokyo (JP)

(72) Inventors: Shoichi Furukawa, Tokyo (JP); Hidehiko Tajima, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 171 days.

(21) Appl. No.: 17/537,829

(22) Filed: Nov. 30, 2021

(65) Prior Publication Data
US 2022/0169585 A1 Jun. 2, 2022

(30) Foreign Application Priority Data

Dec. 2, 2020 (JP) ................................. 2020-200403

(51) Int. Cl.
| | |
|---|---|
| *B01J 8/02* | (2006.01) |
| *B01J 7/00* | (2006.01) |
| *C07C 29/151* | (2006.01) |
| *C01B 3/32* | (2006.01) |
| *B01J 8/00* | (2006.01) |

(52) U.S. Cl.
CPC ............. *C07C 29/1518* (2013.01); *B01J 7/00* (2013.01); *B01J 8/009* (2013.01); *B01J 8/0285* (2013.01); *C01B 3/32* (2013.01); *B01J 2219/00905* (2013.01); *C01B 2203/0211* (2013.01); *C01B 2203/061* (2013.01); *C01B 2203/1241* (2013.01); *C01B 2203/14* (2013.01)

(58) Field of Classification Search
CPC ......... C07C 29/1518; B01J 7/00; B01J 8/009; B01J 8/0285; B01J 2219/00905; C01B 2203/061
USPC ................................. 422/170, 305, 285, 198
See application file for complete search history.

(56) References Cited

U.S. PATENT DOCUMENTS

2018/0354877 A1 12/2018 Sakurai

FOREIGN PATENT DOCUMENTS

| CN | 105836707 A | * | 5/2016 | ............... C01B 3/36 |
|---|---|---|---|---|
| JP | 2017-178810 | | 10/2017 | |
| WO | 2017/094475 | | 6/2017 | |
| WO | 2019/181003 | | 9/2019 | |

OTHER PUBLICATIONS

English Machine Translation of Cn 105836707A, Jiangsu Province Metallurgical Design Institute Co Ltd, May 2016, obtained on Jun. 9, 2023. (Year: 2016).*

* cited by examiner

*Primary Examiner* — Christine T Mui
(74) *Attorney, Agent, or Firm* — Wenderoth, Lind & Ponack, L.L.P.

(57) ABSTRACT

A methanol production system of the present disclosure includes: a reformer including a reaction furnace configured to reform methane in a raw material gas to produce a reformed gas containing CO and $H_2$; a reduced-gas generator configured to reduce $CO_2$ to produce a reduced gas containing CO; and a methanol-containing gas generator configured to produce a methanol-containing gas which contains methanol from a reformed gas produced in the reaction furnace and a reduced gas produced in the reduced-gas generator.

14 Claims, 12 Drawing Sheets

METHANOL PRODUCTION SYSTEM AND METHANOL PRODUCTION METHOD

TECHNICAL FIELD

The present disclosure relates to a methanol production system and a methanol production method. Priority is claimed on Japanese Patent Application No. 2020-200403, filed Dec. 2, 2020, the content of which is incorporated herein by reference.

DESCRIPTION OF RELATED ART

As methods of producing methanol from natural gas containing methane, there is a method of reforming methane in natural gas using a water vapor method or the like, generating a reformed gas containing hydrogen, carbon monoxide, and carbon dioxide, and synthesizing methanol from the reformed gas.

For example, WO2017/094475 describes a methanol production method which includes a reforming gas step of subjecting a raw material gas containing methane to partial oxidation reforming using oxygen to obtain a reformed gas, a $CO/CO_2$ ratio reduction step of reducing a $CO/CO_2$ ratio in the reformed gas, and a production step of obtaining a production gas containing methanol using a reformed gas which has been subjected to the $CO/CO_2$ ratio reduction step.

SUMMARY

At present, further reducing the amount of $CO_2$ to be discharged compared with in the invention described in WO2017/094475 and the water vapor reforming method in the related art is required. Furthermore, in the invention described in WO2017/094475, in order to increase the amount of methanol to be produced, increasing the size of a reformer is required.

The present disclosure was made to solve the above problems, and an object of the present disclosure is to provide a methanol production system and a methanol production method capable of improving the methanol production capacity and reducing the amount of $CO_2$ to be discharged without increasing the size of a reformer.

A methanol production system according to the present disclosure includes: a reformer including a reaction furnace configured to reform methane in a raw material gas to produce a reformed gas containing CO and $H_2$; a reduced-gas generator configured to reduce $CO_2$ to produce a reduced gas containing CO; and a methanol-containing gas generator configured to produce a methanol-containing gas which contains methanol from a reformed gas produced in the reaction furnace and a reduced gas produced in the reduced-gas generator.

A methanol production method according to the present disclosure includes: a reaction step of oxidizing methane in a raw material gas to produce a reformed gas containing CO and $H_2$; a reduced-gas production step of reducing $CO_2$ to produce a reduced gas containing CO; and a methanol-containing gas production step of producing a methanol-containing gas which contains methanol from a reformed gas produced in the reaction step and a reduced gas produced in the reduced-gas production step.

According to the above aspects of the methanol production system and the methanol production method of the present disclosure, it is possible to improve the methanol production capacity and reduce an amount of $CO_2$ to be discharged without increasing the size of a reformer.

DETAILED DESCRIPTION OF EMBODIMENTS

The definitions of the following terms apply throughout the present specification and the claims.
The numerical value ranges represented using the term "to" mean ranges in which the numerical values mentioned before and after the term "to" are included as lower limit values and upper limit values.

First Embodiment

Figure 1:
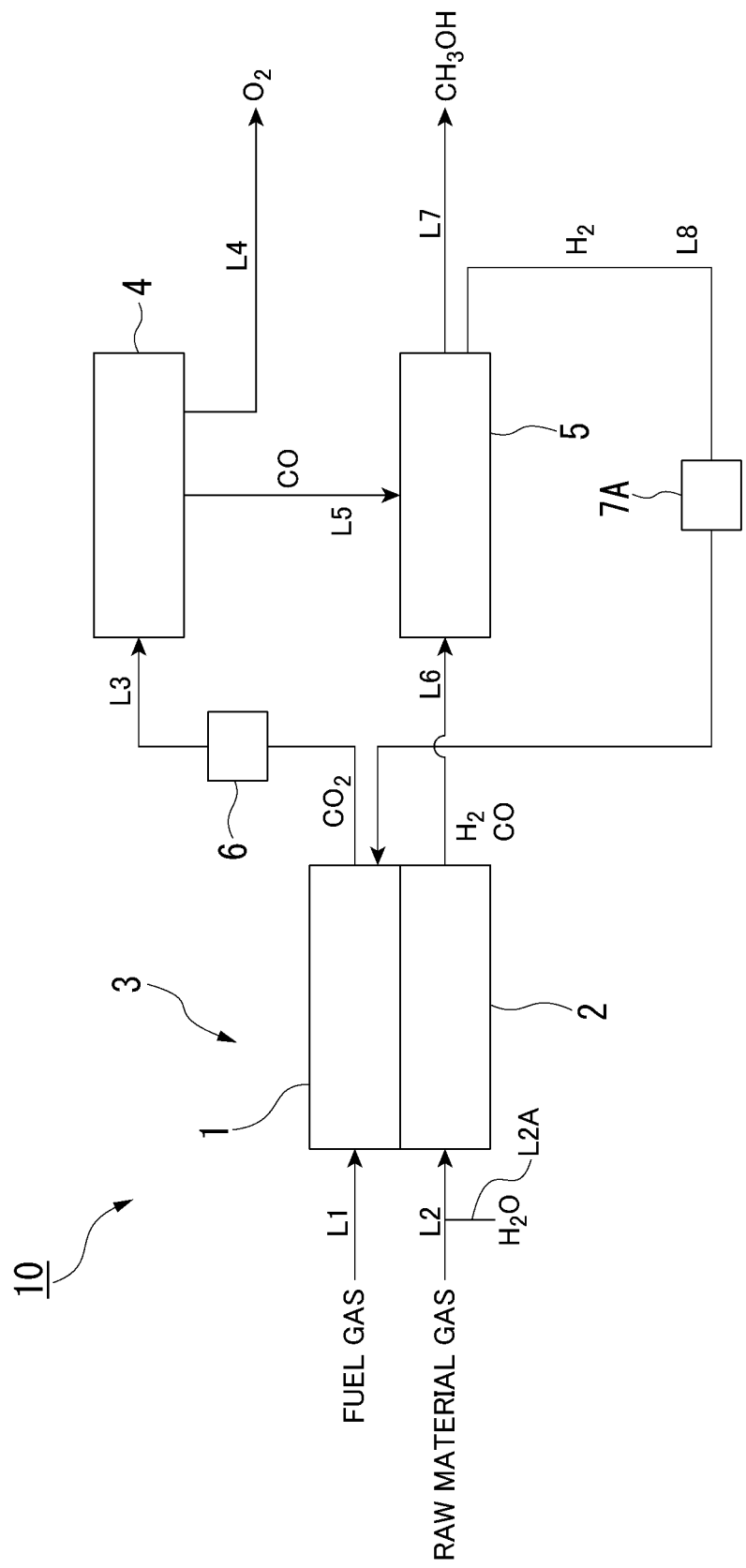
FIG. 1 is a schematic diagram of a methanol production device according to a first embodiment.

As shown in FIG. 1, a methanol production system 10 according to a first embodiment includes a reformer 3 including a combustion furnace 1 and a reaction furnace 2, a reduced-gas generator 4, a methanol-containing gas generator 5, a carbon dioxide separator 6, and a hydrogen separator 7A. Each of the parts will be described below.
(Combustion furnace)
The combustion furnace 1 burns a fuel gas supplied through a line L1 and the excess $H_2$ in producing a methanol-containing gas and supplies the obtained heat to the reaction furnace 2. To be specific, radiant heat generated when a burner in the combustion furnace 1 burns the fuel gas and $H_2$ heats an inside of the reaction furnace 2. Furthermore, the combustion furnace 1 sends an exhaust gas generated at the time of burning the fuel gas and $H_2$ to the carbon dioxide separator 6 through a line L3. The combustion furnace 1 is connected to the line L1 through which a fuel gas is introduced into the combustion furnace 1, the line L3 through which a $CO_2$-containing gas (exhaust gas) is sent to the carbon dioxide separator 6, and a line (hydrogen supply path) L8 through which the excess $H_2$ in producing a methanol-containing gas is introduced respectively.

A fuel gas is not particularly limited as long as it is possible to supply heat through the burning of the fuel gas. Examples of the fuel gas include natural gas, coal gas, coal coke gas, and the like.

(Reaction Furnace)

The reaction furnace 2 reforms a raw material gas containing methane sent through a line L2 and generates a reformed gas containing CO and $H_2$. Here, reforming a raw material gas containing methane ($CH_4$) means generating at least CO and $H_2$ from methane in the raw material gas through a chemical reaction. For example, a catalyst such as a Ni-based catalyst is provided into the reaction furnace 2. A raw material gas and $H_2O$ are supplied into the reaction furnace 2 according to the first embodiment through the line L2. $H_2O$ is supplied to the line L2 through a line L2A. A reformed gas containing CO and $H_2$ generated in the reaction furnace 2 is sent to the methanol-containing gas generator 5 through a line L6. The reaction furnace 2 is connected to the line L2 through which a raw material gas and $H_2O$ are introduced into the reaction furnace 2 and the line L6 through which a reformed gas containing CO and $H_2$ is sent to the methanol-containing gas generator 5 respectively.

(Carbon Dioxide Separator)

The carbon dioxide separator 6 is provided on the line L3. The carbon dioxide separator 6 separates out $CO_2$ in an exhaust gas generated in the combustion furnace 1. The generated $CO_2$ is sent to the reduced-gas generator 4 through the line L3.

A $CO_2$ separation method is not particularly limited, and examples of the $CO_2$ separation method include a chemical absorption method, a membrane separation method, a pressure fluctuation adsorption method, and the like. In the chemical absorption method, $CO_2$ in an exhaust gas is absorbed using an amine absorbing liquid, and then $CO_2$ is separated out from the amine absorbing liquid by heating the amine absorbing liquid having $CO_2$ absorbed therein. In the membrane separation method, an exhaust gas is caused to be passed through an inorganic separation membrane so that $CO_2$ is selectively separated out. In the pressure fluctuation adsorption method, $CO_2$ is separated out by removing a gas which is easily adsorbed by increasing and decreasing a pressure by utilizing the fact that the adsorption capacity differs in accordance with a partial pressure of a gas to be adsorbed.

(Reduced-Gas Generator)

The reduced-gas generator 4 generates a reduced gas containing CO by reducing $CO_2$ sent through the line L3. The reduced-gas generator 4 in the first embodiment is an electrolytic device which includes a positive electrode (not shown), a negative electrode (not shown), and an electrolyte substance (not shown). The reduced-gas generator 4 sends the reduced gas containing CO to the methanol-containing gas generator 5 through a line L5. Furthermore, the reduced-gas generator 4 releases $O_2$ generated together with the reduced gas containing CO into the atmosphere through a line L4. The reduced-gas generator 4 is connected to the line L3 through which $CO_2$ is introduced, the line L5 through which a reduced gas generated in the reduced-gas generator 4 is introduced into the methanol-containing gas generator 5, and the line L4 through which generated $O_2$ is discharged respectively.

At the positive electrode, $O_2$ is generated. A catalyst may be used for the positive electrode to promote an electrolytic reaction. Catalyst materials used for the positive electrode include a metal such as platinum, palladium, and nickel, an alloy containing these, a binary metal oxide such as manganese oxide, nickel oxide, cobalt oxide, iron oxide, tin oxide, indium oxide, iridium oxide, and ruthenium oxide, ternary metal oxide such as Ni—Co—O and Ni—Fe—O, or a metal complex such as a Ru complex. Furthermore, a catalyst solution containing the metal complex or the like dissolved therein may be brought into contact with the positive electrode.

At the negative electrode, a reduced gas containing CO is generated due to a reduction reaction of $CO_2$. A catalyst may be used for the negative electrode to promote an electrolytic reaction. The catalyst used for the negative electrode includes a metal such as gold, silver, platinum, palladium, nickel, cobalt, iron, manganese, titanium, cadmium, zinc, indium, or gallium, an alloy containing these metals, a carbon material such as graphene and carbon nanotubes, a metal complex such as a Ru complex, or the like. Furthermore, a catalyst solution containing the metal complex or the like dissolved therein may be brought into contact with the negative electrode.

It is preferable that the electrolyte substance used for the electrolytic device be an aqueous solution containing an arbitrary electrolyte, an ionic liquid, an organic solvent, an organic electrolyte solution, or a solid electrolyte including an ionic conductive membrane or an ionic conductive ceramic. It is preferable that the aqueous solution containing an electrolyte be, for example, an aqueous solution which contains at least one of hydroxide ions, hydrogen ions, potassium ions, sodium ions, lithium ions, chloride ions, bromide ions, iodide ions, nitrate ions, sulfate ions, or phosphate ions.

A method for introducing $CO_2$ into the reduced-gas generator 4 may be, but is not particularly limited to, introduced in a gaseous state or may be introduced in a state in which $CO_2$ is absorbed using an absorbing liquid. When $CO_2$ is absorbed using the absorbing liquid, CO may be taken out from the absorbing liquid which has been subjected to reduction.

(Methanol-Containing Gas Generator)

The methanol-containing gas generator 5 generates a methanol-containing gas which contains methanol from a reformed gas generated in the reaction furnace 2 in the reformer 3 and a reduced gas generated in the reduced-gas generator 4. The generated methanol is moved into a storage tank (not shown) through a line L7 and stored in the storage tank (not shown). The methanol-containing gas generator 5 is connected to the line L6 through which a reformed gas is introduced, the line L5 through which a reduced gas is introduced, the line L7 through which methanol is stored, and a line (hydrogen supply path) L8 through which the excess $H_2$ in generating a methanol-containing gas is introduced into the combustion furnace 1 respectively.

The methanol-containing gas generator 5 may be any device which can synthesize methanol from the reformed gas and the reduced gas. Examples of the methanol-containing gas generator 5 include reactors such as a fixed bed type, a fluidized bed type, and a jet bed type, micro-channel reactors, isothermal reactors, and the like. Among them, a fluidized bed type reactor, a jet bed type reactor, a micro-channel reactor, and an isothermal reactor are preferable and an isothermal reactor is more preferable. If the methanol-containing gas generator 5 is an isothermal reactor, it is possible to control the local occurrence of high temperature inside the device to homogenize the heat and reduce a load on the device itself, a methanol synthesis catalyst for synthesizing methanol, and the like.

(Hydrogen Separator)

The hydrogen separator 7A is provided in the middle of the line (hydrogen supply path) L8, separates out the excess $H_2$ in generating the methanol-containing gas generated in the methanol-containing gas generator 5, and supplies $H_2$ into the combustion furnace 1. Examples of the hydrogen separator include a Pd alloy membrane, a porous ceramic membrane, and the like.

"Methanol Production Method"

Figure 2:
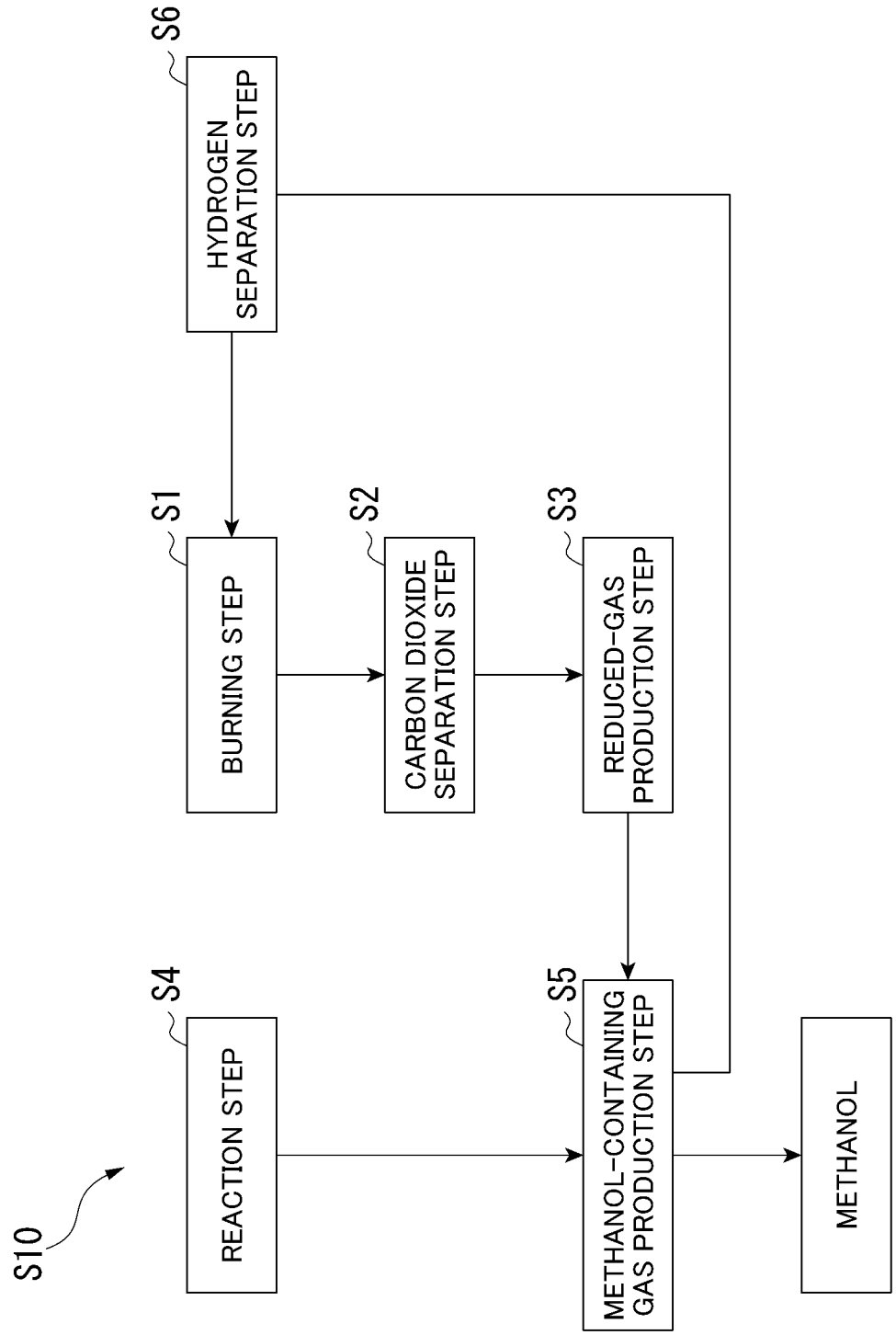
FIG. 2 is a flowchart of a methanol production method according to the first embodiment.

A methanol production method in the first embodiment will be described below. As shown in FIG. 2, a methanol production method S10 includes a combustion step S1, a carbon dioxide separation step S2, a reduced-gas production step S3, a reaction step S4, a methanol-containing gas production step S5, and a hydrogen separation step S6. Each of the steps will be described below.

(Combustion Step)

In the combustion step S1, the heat used in the reaction step S4 is generated by burning the excess $H_2$ in generating a fuel gas and a methanol-containing gas in the combustion furnace 1. Furthermore, in the combustion step S1, exhaust gas is generated through burning of a fuel gas. When the fuel gas is natural gas containing methane, a combustion reaction is represented by the following Expression (1). Here, examples of a supply source of $O_2$ include air in the atmosphere. Furthermore, the burning of $H_2$ is represented by the following Expression (2). Here, the generated heat is used in the reaction step S4. In addition, the exhaust gas generated in burning a fuel gas is sent to the carbon dioxide separator 6 through the line L3:

$$CH_4 + 2O_2 \rightarrow CO_2 + 2H_2O + 802 \text{ kJ/mol} \tag{1}$$

$$H_2 + \tfrac{1}{2}O_2 \rightarrow H_2O + 240 \text{ kJ/mol} \tag{2}$$

The fuel gas used in the combustion step S1 is preferably 10% by mass to 20% by mass when a total amount of a raw material gas and a fuel gas is assumed to be 100% by mass. If the fuel gas is in the above range, it is possible to efficiently produce methanol while minimizing an amount of $CO_2$ to be generated. Furthermore, the excess $H_2$ in the methanol-containing gas production step S5 is preferably 25% by mass to 35% by mass with respect to hydrogen to be produced. If the amount of $H_2$ is within this range, it is possible to supply the heat required for the reaction while reducing the amount of fuel gas.

(Carbon Dioxide Separation Step)

In the carbon dioxide separation step S2, $CO_2$ is separated out from the exhaust gas generated in the combustion step S1. The separated out $CO_2$ is sent to the reduced-gas generator 4 through the line L3.

(Reduced-Gas Production Step)

In the reduced-gas production step S3, $CO_2$ separated out in the carbon dioxide separation step S2 is reduced to generate a reduced gas containing CO. The reduced-gas generator 4 reduces $CO_2$ to CO through an electrolytic reduction reaction. A specific reaction is represented by the following Expression (3):

$$CO_2 \rightarrow CO + \tfrac{1}{2}O_2 \tag{3}$$

An electrolytic voltage (vs. SHE) in the foregoing Expression (3) is 1.29 V. Here, vs. SHE means a potential using a hydrogen electrode (0 V) as a reference. CO generated in this reaction is generated at the negative electrode and $O_2$ is generated at the positive electrode. The CO generated in the negative electrode is sent to the methanol-containing gas generator 5 through the line L5. $O_2$ generated at the positive electrode is released into the atmosphere through the line L4.

The entire amount of the reduced gas produced in the reduced-gas production step S3 is used in the methanol-containing gas production step S5. When the reduced gas is used in the methanol-containing gas production step S5, it is possible to increase the reaction rate.

(Reaction Step)

In the reaction step S4, an inlet temperature of the reaction furnace 2 of the reformer 3 is 450° C. to 650° C. and an outlet temperature is 700° C. to 950° C. A reaction pressure is 1 to 2 MPa. The heat supplied from the combustion furnace 1 is used for raising the outlet temperature of the reaction furnace 2 and maintaining reaction heat. Reaction expressions when methane is reformed using water vapor are represented by the following Expressions (4) and (5):

$$CH_4 + H_2O \rightarrow CO + 3H_2 - 205.9 \text{ kJ/mol} \tag{4}$$

$$CH_4 + 2H_2O \rightarrow CO_2 + 4H_2 + 165.1 \text{ kJ/mol} \tag{5}$$

Here, the reformed gas containing the generated CO and $H_2$ is sent to the methanol-containing gas generator 5 through the line L6.

The raw material gas used in the reaction step S4 is preferably 80% by mass to 90% by mass when a total amount of the raw material gas and the fuel gas is assumed to be 100% by mass. If the amount of raw material gas is within the above range, it is possible to efficiently produce methane while minimizing the amount of $CO_2$ to be generated.

(Methanol-Containing Gas Production Step)

In the methanol-containing gas production step S5, methanol-containing gas which contains methanol is produced from the reformed gas produced in the reaction step S4 and the reduced gas produced in the reduced-gas production step S3. Methanol synthesis expressions are represented by the following Expression (6) and (7). As represented in the following Expressions (6) and the foregoing Expression (4), $H_2$ produced in the reduced-gas production step S3 is also left after methanol synthesis. The excess $H_2$ which is left is sent to the hydrogen separator 7A through the line (hydrogen supply path) L8. The synthesized methanol is stored through the line L7:

$$CO + 2H_2 \rightarrow CH_3OH \tag{6}$$

$$CO_2 + 3H_2 \rightarrow CH_3OH + H_2O \tag{7}$$

When the methanol-containing gas generator 5 is an isothermal reactor, it is possible to prevent a local temperature rise in the device and it is possible to make the temperature uniform and perform control such that the uniform temperature within a preferable range. Thus, it is possible to reduce the load applied to a catalyst and the like due to the heat of a synthesis reaction. The temperature required for a methanol synthesis is 100° C. to 300° C., and preferably 150° C. to 250° C.

(Hydrogen Separation Step)

In the hydrogen separation step S6, the excess hydrogen left in the methanol synthesis in the methanol-containing gas production step S5 is separated out. The separated-out $H_2$ is sent to the combustion furnace 1 through the line (hydrogen supply path) L8.

(Action and Effect)

In the first embodiment described above, when $CO_2$ in the exhaust gas generated through burning is used as a raw material for methanol, it is possible to increase the amount of methanol to be produced while reducing the amount of $CO_2$ releasing into the atmosphere, without increasing the size of the reformer. Furthermore, when the excess hydrogen left in the methanol synthesis is used for burning, it is possible to supply the heat required for reforming methane while further reducing the amount of $CO_2$. In addition, when increase rates of the raw material gas, the fuel gas, and the excess hydrogen are adjusted, it is possible to produce methanol without releasing $CO_2$ into the atmosphere.

Although the raw material gas is introduced into the reaction furnace 2 as it is in the first embodiment, a sulfur removing facility (not shown) may be provided on an upstream side of the reaction furnace 2, sulfur compounds which minimizes the reaction of a catalyst may be removed from a raw material gas, and then the raw material gas may be introduced into the reaction furnace 2.

Although the methanol-containing gas is stored as it is in the first embodiment, a methanol-containing gas may be sent to a methanol separation device (not shown) through the line L7 and high-purity methanol may be produced through distilling.

Although a separator is not used in the reduced-gas generator 4 in the first embodiment, a separator may be used. As the separator, it is possible to use a porous membrane, an electrolyte membrane, or the like.

Although water vapor reforming is used in the reaction furnace 2 in the first embodiment, a methane reforming reaction is not limited to water vapor reforming. For example, as the methane reforming reaction, a $CO_2$ reforming method, a reverse shift reaction method, a direct contact partial oxidation method, a self-thermal reforming method, a non-catalytic partial oxidation method, and the like can be used.

Although the exhaust gas of the combustion furnace 1 is used as a raw material for producing a reduced gas in the first embodiment, the methanol production system 10 in the first embodiment is not limited to the exhaust gas of the combustion furnace 1. For example, the exhaust gas may be an exhaust gas generated in an auxiliary facility for generating steam ($H_2O$), a gas turbine generator (GTG) for supplying electric power, or the like.

Although an electrolytic device is used for the reduced-gas generator in the first embodiment, the reduced-gas generator 4 is not limited to the electrolytic device. For example, the reduced-gas generator may be a solid oxide type electrolytic cell using a solid oxide electrolyte or an artificial photosynthesis device which includes a photocatalyst.

Although the excess $H_2$ in producing a methanol-containing gas is used for burning in the first embodiment, heat may be supplied to the reaction furnace 2 using another type of energy such as renewable energy instead of $H_2$.

Second Embodiment

Figure 3:
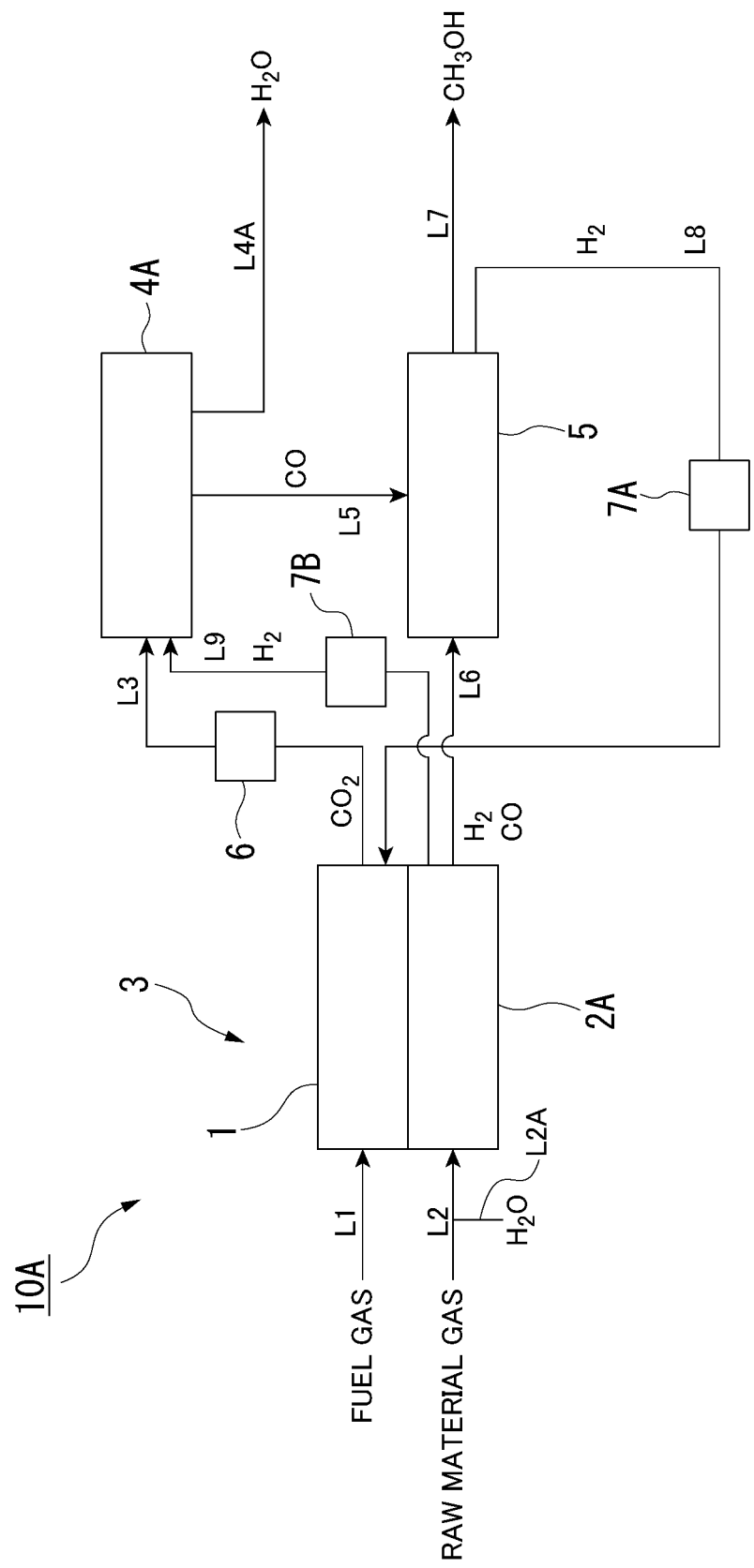
FIG. 3 is a schematic diagram of a methanol production device according to a second embodiment.

A second embodiment will be described below with reference to FIG. 3. A methanol production system 10A according to the second embodiment includes a reformer 3 including a combustion furnace 1 and a reaction furnace 2A, a reduced-gas generator 4A, a methanol-containing gas generator 5, a carbon dioxide separator 6, a hydrogen separator 7A, and a hydrogen separator 7B. Constituent elements in the second embodiment that are similar to those of the first embodiment are distinguished from those of the first embodiment by attaching different letters after the same reference numerals. Here, among the similar constituent elements, when they have substantially the same functional constitutions as constituent elements which have been described, description of these constituent elements will be omitted. Each part will be described below.

(Reaction Furnace)

The reaction furnace 2A reforms a raw material gas containing methane sent through a line L2 and produces a reformed gas containing CO and $H_2$. For example, a catalyst such as a Ni-based catalyst is provided in the reaction furnace 2A. The raw material gas and $H_2O$ are supplied to the reaction furnace 2A according to the second embodiment through the line L2. $H_2O$ is supplied to the line L2 through a line L2A. The reformed gas containing CO and $H_2$ produced in the reaction furnace 2A is sent to the methanol-containing gas generator 5 through a line L6. Furthermore, a part of the reformed gas is sent to the hydrogen separator 7B through a line (reformed-gas introduction path) L9. The reaction furnace 2A is connected to the line L2 through which the raw material gas and $H_2O$ are introduced into the reaction furnace 2A, the line L6 through which the reformed gas containing CO and $H_2$ is sent to the methanol-containing gas generator 5, and the line (reformed-gas introduction path) L9 through which a part of the reformed gas is sent to the hydrogen separator 7B respectively.

(Hydrogen Separator)

The hydrogen separator 7B is provided in the middle of the line (reformed-gas introduction path) L9, separates out $H_2$ in the reformed gas produced in the reaction furnace 2A, and supplies $H_2$ to the reduced-gas generator 4A. Examples of the hydrogen separator include a Pd alloy membrane, a porous ceramic membrane, and the like.

(Reduced-Gas Generator)

The reduced-gas generator 4A produces CO-containing reduced gas and $H_2O$ from $CO_2$ sent through a line L3 and $H_2$ sent through the line (reformed-gas introduction path) L9. The reduced-gas generator 4A in the second embodiment is an electrolytic device which includes a positive electrode (not shown), a negative electrode (not shown), and an electrolyte substance (not shown). The reduced-gas generator 4A sends the reduced gas containing CO to the methanol-containing gas generator 5 through a line L5. Furthermore, the reduced-gas generator 4A releases $H_2O$ produced together with the reduced gas containing CO as a waste liquid through a line L4A. The reduced-gas generator 4A is connected to the line L3 through which $CO_2$ is introduced, the line L5 through which the reduced gas produced in the reduced-gas generator 4A is introduced into the methanol-containing gas generator 5, the line L4A through which the produced $H_2O$ is discharged, and the line (reformed-gas introduction path) L9 through which $H_2$ is introduced respectively.

At the positive electrode, $H_2$ sent from the hydrogen separator 7B is oxidized to produce $H_2O$. A catalyst may be used for the positive electrode to promote an electrolytic reaction. A catalyst material used for the positive electrode includes a metal such as platinum, palladium, and nickel, an alloy containing these, a binary metal oxide such as manganese oxide, nickel oxide, cobalt oxide, iron oxide, tin oxide, indium oxide, iridium oxide, and ruthenium oxide, a ternary metal oxide such as Ni—Co—O and Ni—Fe—O, and a metal complex such as a Ru complex. Furthermore, a catalyst solution containing the metal complex or the like dissolved therein may be brought into contact with the positive electrode.

At the negative electrode, the reduced gas containing CO is produced through a $CO_2$ reduction reaction. A catalyst may be used for the negative electrode to promote an electrolytic reaction. The catalyst used for the negative electrode includes a metal such as gold, silver, platinum, palladium, nickel, cobalt, iron, manganese, titanium, cadmium, zinc, indium, or gallium, an alloy containing these metals, a carbon material such as graphene and carbon nanotubes, a metal complex such as a Ru complex, or the like. Furthermore, for example, a catalyst solution containing the metal complex or the like dissolved therein may be brought into contact with the negative electrode.

It is preferable that the electrolyte substance used in the electrolytic device be an aqueous solution containing an arbitrary electrolyte, an ionic liquid, an organic solvent, an organic electrolyte solution, or a solid electrolyte including an ionic conductive membrane or an ionic conductive ceramic. It is preferable that the aqueous solution containing an electrolyte be, for example, an aqueous solution which contains at least one of hydroxide ions, hydrogen ions, potassium ions, sodium ions, lithium ions, chloride ions, bromide ions, iodide ions, nitrate ions, sulfate ions, phosphate ions, or the like.

"Methanol Production Method"

Figure 4:
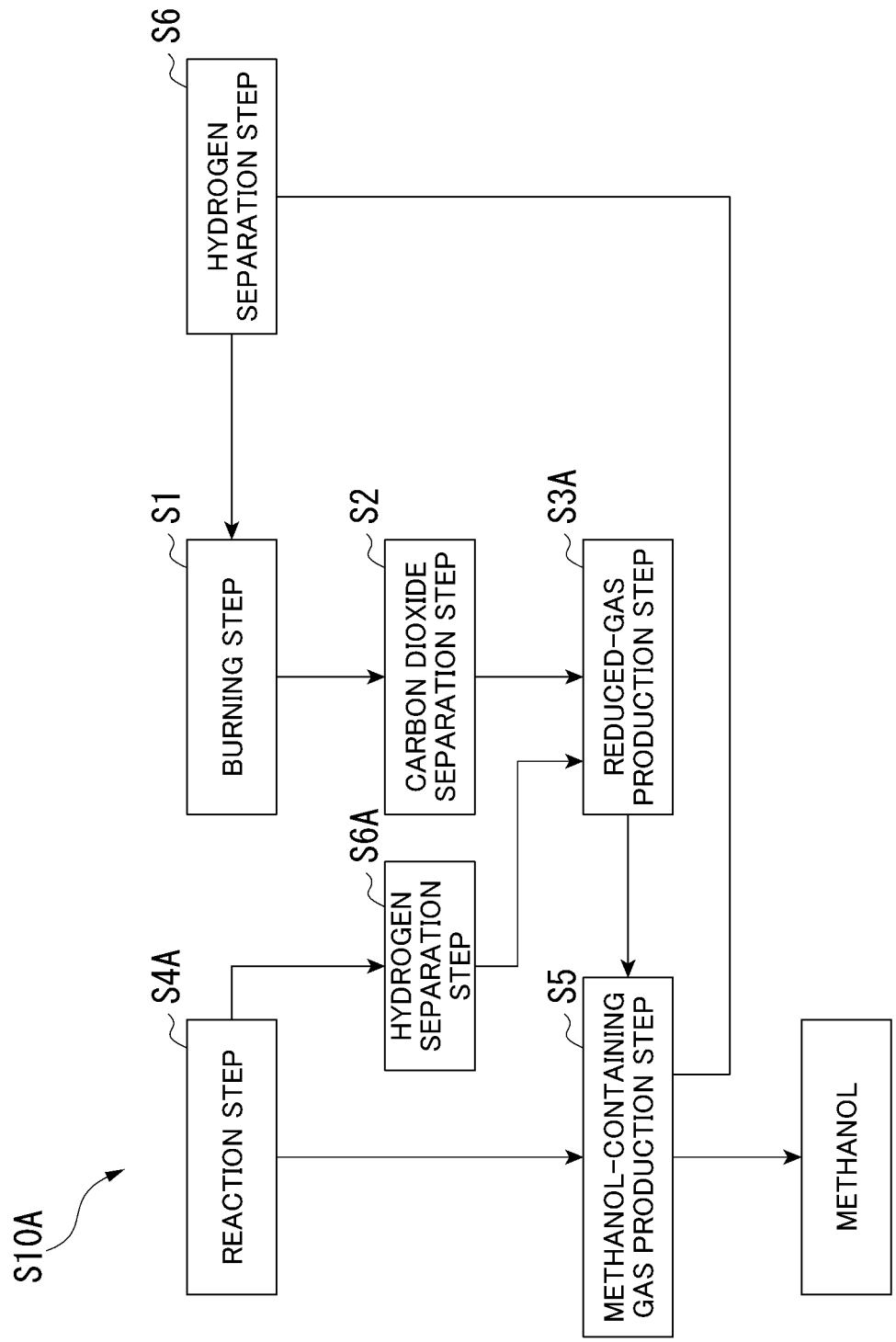
FIG. 4 is a flowchart of a methanol production method according to the second embodiment.

A methanol production method in the second embodiment will be described below. As shown in FIG. 4, a methanol production method S10A includes a combustion step S1, a carbon dioxide separation step S2, a reduced-gas production step S3A, a reaction step S4A, a methanol-containing gas production step S5, a hydrogen separation step S6, and a hydrogen separation step S6A. Constituent elements in the second embodiment that are similar to those of the first embodiment are distinguished from those of the first embodiment by attaching different letters after the same reference numerals. Here, among the similar constituent elements, when they have substantially the same functional constitutions as constituent elements which have been described, description of these constituent elements will be omitted. Each step will be described below.

(Reaction Step)

In the reaction step S4A, an inlet temperature of the reaction furnace 2A of the reformer 3 is 450° C. to 650° C. and an outlet temperature is 700° C. to 950° C. A reaction pressure is 1 to 2 MPa. The heat supplied from the combustion furnace 1 is used for rising the outlet temperature of the reaction furnace 2A and maintaining the reaction heat. Reaction expressions when methane is reformed using water vapor are represented by the foregoing Expressions (4) and (5).

Here, the reformed gas containing the generated CO and $H_2$ is sent to the methanol-containing gas generator 5 through the line L6 and a part of the reformed gas is sent to the hydrogen separator 7B through the line (reformed-gas introduction path) L9.

The raw material gas used in the reaction step S4A is preferably 80% by mass to 90% by mass when a total amount of the raw material gas and the fuel gas is assumed to be 100% by mass. If the amount of raw material gas is within the above range, it is possible to efficiently produce methanol while minimizing the amount of $CO_2$ to be generated. If $H_2$ contained in a part of the reformed gas sent to the reduced-gas generator 4A is 10% of a total amount of $H_2$ produced, it is possible to efficiently progress an electrolytic reaction of the reduced-gas generator 4A.

(Hydrogen Separation Step)

In the hydrogen separation step S6A, $H_2$ is separated out from a part of the reformed gas produced in the reaction step S4A. The separated-out $H_2$ is sent to the reduced-gas generator 4A through the line (reformed-gas introduction path) L9 and is used for a $CO_2$ reduction reaction.

(Reduced-Gas Production Step)

In the reduced-gas production step S3A, $CO_2$ separated out in the carbon dioxide separation step S2 is reduced to produce a reduced gas containing CO. In the case of the reduced-gas generator 4A, CO and $H_2O$ are produced from $H_2$ and $CO_2$. A specific reaction is represented by the following Expression (8):

$$CO_2 + H_2 \rightarrow CO + H_2O \qquad (8).$$

An electrolytic voltage in the foregoing Expression (8) is −0.31 V. Therefore, the methanol production system 10A according to the second embodiment can produce a reduced gas at a voltage lower than that of the methanol production system 10 according to the first embodiment. CO generated in this reaction is generated at the negative electrode and $H_2O$ is generated at the positive electrode. The CO generated at the negative electrode is sent to the methanol-containing gas generator 5 through the line L5. The $H_2O$ generated at the positive electrode is discharged through the line L4A as a waste liquid.

(Action and Effect)

In the second embodiment described above, when $CO_2$ in the exhaust gas generated through burning is used as a raw material for methanol, it is possible to increase the amount of methanol to be produced while reducing the amount of $CO_2$ releasing into the atmosphere, without increasing the size of the reformer. Furthermore, when the excess hydrogen left in the reaction step S4A is used in the reduced-gas production step S3A, it is possible to produce the reduced gas with power consumption lower than that in the first embodiment.

Third Embodiment

Figure 5:
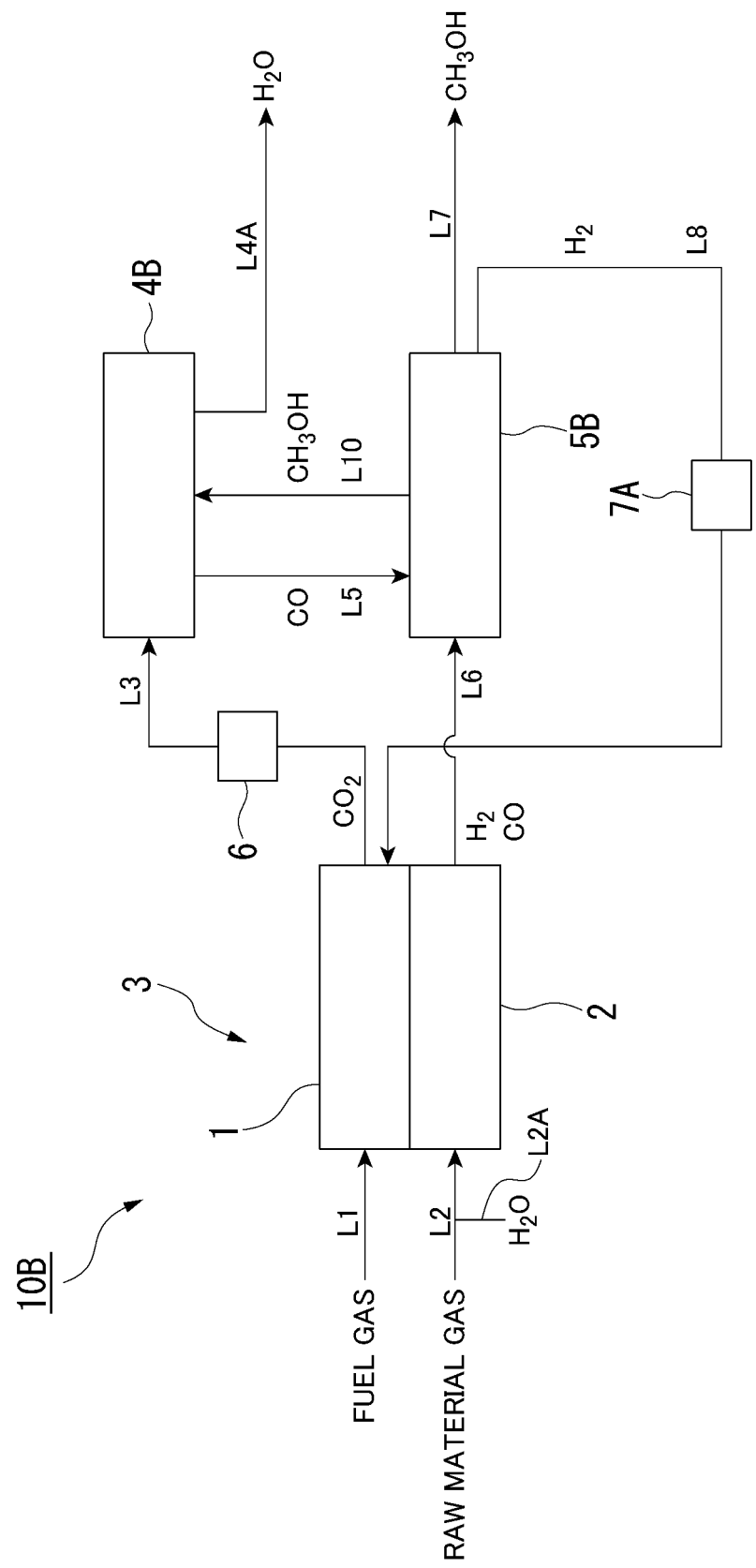
FIG. 5 is a schematic diagram of a methanol production device according to a third embodiment.

A third embodiment will be described below with reference to FIG. 5. A methanol production system 10B according to the third embodiment includes a reformer 3 including a combustion furnace 1 and a reaction furnace 2, a reduced-gas generator 4B, a methanol-containing gas generator 5B, a carbon dioxide separator 6, and a hydrogen separator 7A. In the following description, constituent elements in the third embodiment that are similar to those of the first embodiment and the second embodiment are distinguished from those of the first embodiment and the second embodiment by attaching different letters after the same reference numerals. Here, among the similar constituent elements, when they have substantially the same functional constitutions as constituent elements which have been described, a description of these constituent elements will be omitted. Each step will be described below.

(Reduced-Gas Generator)

The reduced-gas generator 4B produces $H_2O$ and a reduced gas containing CO from $CO_2$ sent through a line L3 and methanol-containing gas sent from the methanol-containing gas generator 5B. The reduced-gas generator 4B in the third embodiment is an electrolytic device which includes a positive electrode (not shown), a negative electrode (not shown), and an electrolyte substance (not shown). The reduced-gas generator 4B sends the reduced gas containing CO to the methanol-containing gas generator 5 through a line L5. The methanol-containing gas sent to the reduced-gas generator 4B is preferably 10 to 20% by mass of the produced methanol-containing gas. Furthermore, the reduced-gas generator 4B releases $H_2O$ produced together with the reduced gas containing CO as a waste liquid through a line L4A. The reduced-gas generator 4B is connected to the line L3 through which $CO_2$ is introduced into the reduced-gas generator 4B, the line L5 through which the reduced gas produced in the reduced-gas generator 4B is introduced into the methanol-containing gas generator 5B, the line L4A through which the produced $H_2O$ is discharged, and a line (methanol introduction path) L10 through which the methanol-containing gas is introduced into the reduced-gas generator 4B respectively.

At the positive electrode, methanol in the methanol-containing gas sent from the methanol-containing gas generator 5B is oxidized to produce $H_2O$ and $CO_2$. The produced $CO_2$ is sent to the negative electrode. A catalyst may be used for the positive electrode to promote an electrolytic reaction. The catalyst material used for the positive electrode includes a metal such as rhodium, platinum, palladium, and nickel, an alloy containing these, a binary metal oxide such as platinum oxide, manganese oxide, nickel oxide, cobalt oxide, iron oxide, tin oxide, indium oxide, iridium oxide, and ruthenium oxide, a ternary metal oxide such as Ni—Co—O and Ni—Fe—O, and a metal complex such as a Ru complex. Furthermore, a catalyst solution containing the metal complex or the like dissolved therein may be brought into contact with the positive electrode.

At the negative electrode, a reduced gas containing CO is produced through a $CO_2$ reduction reaction. A catalyst may be used for the negative electrode to promote an electrolytic reaction. The catalyst used for the negative electrode includes a metal such as gold, silver, platinum, palladium, nickel, cobalt, iron, manganese, titanium, cadmium, zinc, indium, and gallium, an alloy containing these metals, a carbon material such as graphene and carbon nanotubes, a metal complex such as a Ru complex, and the like. Furthermore, for example, a catalyst solution containing the metal complex or the like dissolved therein may be brought into contact with the negative electrode.

It is preferable that the electrolyte substance used in the electrolytic device be an aqueous solution containing an arbitrary electrolyte, an ionic liquid, an organic solvent, an organic electrolyte solution, or a solid electrolyte including an ionic conductive membrane or an ionic conductive ceramic. It is preferable that the aqueous solution containing an electrolyte be, for example, an aqueous solution which contains at least one of hydroxide ions, hydrogen ions, potassium ions, sodium ions, lithium ions, chloride ions, bromide ions, iodide ions, nitrate ions, sulfate ions, phosphate ions, and the like.

(Methanol-Containing Gas Generator)

The methanol-containing gas generator 5B produces a methanol-containing gas which contains methanol from the reformed gas produced in the reaction furnace 2 in the reformer 3 and the reduced gas produced in the reduced-gas generator 4B. The produced methanol is moved and stored in a storage tank (not shown) through the line L7. Furthermore, the methanol-containing gas generator 5B sends a part of the produced methanol-containing gas to the reduced-gas generator 4B through the line (methanol introduction path) L10. The methanol-containing gas generator 5 is connected to the line L6 through which the reformed gas is introduced, the line L5 through which the reduced gas is introduced into the methanol-containing gas generator 5B, the line L7 through which methanol is stored, the line (hydrogen supply path) L8 through which the excess $H_2$ in producing the methanol-containing gas is introduced into the combustion furnace 1, and the line (methanol introduction path) L10 through which a part of the produced methanol-containing gas is introduced into the reduced-gas generator 4B respectively.

"Methanol Production Method"

Figure 6:
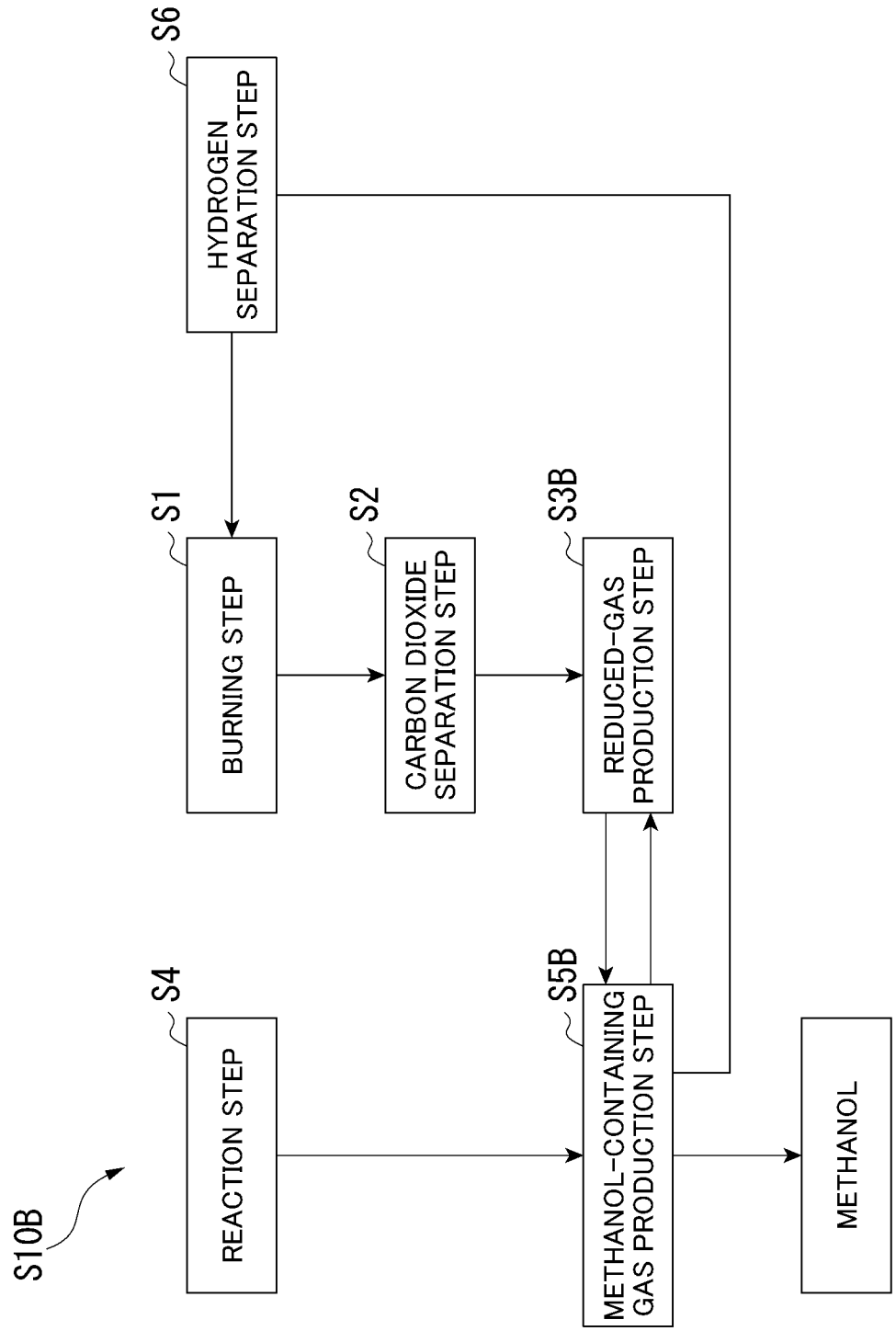
FIG. 6 is a flowchart of a methanol production method according to the third embodiment.

A methanol production method in the third embodiment will be described below. As shown in FIG. 6, a methanol production method S10B includes a combustion step S1, a carbon dioxide separation step S2, a reduced-gas production step S3B, a reaction step S4, a methanol-containing gas production step S5B, and a hydrogen separation step S6. In the following description, constituent elements in the third embodiment that are similar to those of the first embodiment and the second embodiment are distinguished from those of the first embodiment and the second embodiment by attaching different letters after the same reference numerals. Here, among the similar constituent elements, when they have substantially the same functional constitutions as constituent elements which have been described, description of these constituent elements will be omitted. Each step will be described below.

(Methanol-Containing Gas Production Step)

In the methanol-containing gas production step S5B, a methanol-containing gas which contains methanol is produced from the reformed gas produced in the reaction step S4 and the reduced gas produced in the reduced-gas production step S3B. Methanol synthesis expressions are represented by the foregoing Expressions (6) and (7). As represented by the foregoing Expressions (6) and (4), a part of $H_2$ produced in the reduced-gas production step S3 is also left after the synthesis of methanol. The excess $H_2$ which is left is sent to the hydrogen separator 7A through the line (hydrogen supply path) L8. Furthermore, the produced methanol-containing gas is stored through the line L7 and a part of the methanol-containing gas is sent to the reduced-gas generator 4B through the line (methanol introduction path) L10.

(Reduced-Gas Production Step)

In the reduced-gas production step S3B, $CO_2$ separated out in the carbon dioxide separation step S2 is reduced to produce a reduced gas containing CO. In the case of the reduced-gas generator 4B, CO and $H_2O$ is produced from the methanol-containing gas and $CO_2$. A specific reaction is represented by the following Expression (9). A reaction at the positive electrode is represented by the following Expression (10) and a reaction at the negative electrode is represented by the following Expression (11):

$$2CO_2 + CH_3OH \rightarrow 3CO + 2H_2O \qquad (9)$$

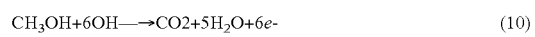

$$CH_3OH + 6OH^- \rightarrow CO_2 + 5H_2O + 6e^- \qquad (10)$$

$$H_2O + CO_2 + 2e^- \rightarrow CO + 2OH^- \qquad (11).$$

An electrolytic voltage in the foregoing Expression (9) is 0.12 V. Therefore, the methanol production system 10B according to the third embodiment can produce a reduced gas at a voltage lower than that of the methanol production system 10 according to the first embodiment. CO generated in this reaction is generated at the negative electrode and $H_2O$ is generated at the positive electrode. The CO generated at the negative electrode is sent to the methanol-containing gas generator 5 through the line L5. The $H_2O$ generated at the positive electrode is discharged through the line L4A as a waste liquid.

(Action and Effect)

In the third embodiment described above, when $CO_2$ in the exhaust gas generated through burning is used as a raw material for methanol, it is possible to increase the amount of methanol to be produced while reducing the amount of $CO_2$ releasing into the atmosphere, without increasing the size of the reformer. Furthermore, when a part of the methanol-containing gas produced in the methanol-containing gas generator 5B is used in the reduced-gas production step S3B, it is possible to produce a reduced gas with power consumption lower than that in the first embodiment.

Fourth Embodiment

Figure 7:
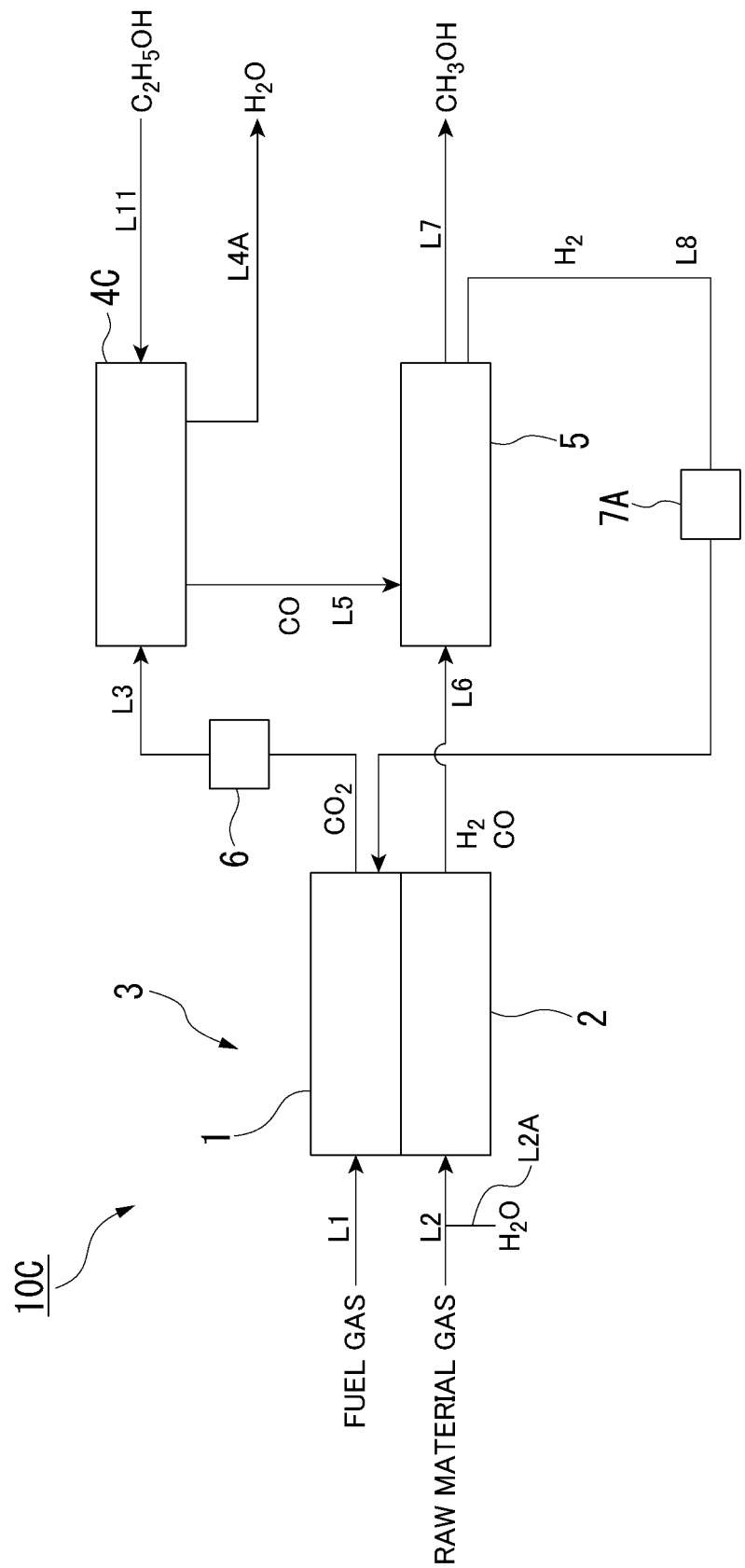
FIG. 7 is a schematic diagram of a methanol production device according to a fourth embodiment.

A fourth embodiment will be described below with reference to FIG. 7. A methanol production system 10C according to the fourth embodiment includes a reformer 3 including a combustion furnace 1 and a reaction furnace 2, a reduced-gas generator 4C, a methanol-containing gas generator 5, a carbon dioxide separator 6, and a hydrogen separator 7A. In the following description, constituent elements in the fourth embodiment that are similar to those of the first embodiment, the second embodiment, and the third embodiment are distinguished from those of the first embodiment, the second embodiment, and the third embodiment by attaching different letters after the same reference numerals. Here, among the similar constituent elements, when they have substantially the same functional constitutions as constituent elements which have been described, description of these constituent elements will be omitted. Each step will be described below.

(Reduced-Gas Generator)

The reduced-gas generator 4C produces $H_2O$ and a reduced gas containing CO from $CO_2$ sent through a line L3 and ethanol sent through a line L11. It is preferable that the ethanol introduced from the line L11 be bio-ethanol. The reduced-gas generator 4C in the fourth embodiment is an electrolytic device which includes a positive electrode (not shown), a negative electrode (not shown), and an electrolyte substance (not shown). The reduced-gas generator 4C sends the reduced gas containing CO to the methanol-containing gas generator 5 through the line L5. Furthermore, the reduced-gas generator 4C releases $H_2O$ produced together with the reduced gas containing CO through a line L4A as a waste liquid. The reduced-gas generator 4C is connected to the line L3 through which $CO_2$ is introduced into the reduced-gas generator 4C, the line L5 through which the reduced gas produced in the reduced-gas generator 4C is introduced into the methanol-containing gas generator 5, the line L4A through which the produced $H_2O$ is discharged, and the line L11 through which ethanol is introduced into the reduced-gas generator 4C respectively.

At the positive electrode, ethanol introduced through the line L11 is oxidized to produce $H_2O$ and $CO_2$. The produced $CO_2$ is sent to the negative electrode. A catalyst may be used for the positive electrode to promote an electrolytic reaction. A catalyst material used for the positive electrode includes a metal such as rhodium, platinum, palladium, and nickel, an alloy containing these, a binary metal oxide such as platinum oxide, manganese oxide, nickel oxide, cobalt oxide, iron oxide, tin oxide, indium oxide, iridium oxide, and ruthenium oxide, a ternary metal oxide such as Ni—Co—O and Ni—Fe—O, and a metal complex such as a Ru complex. Furthermore, a catalyst solution containing the metal complex or the like dissolved therein may be brought into contact with the positive electrode.

At the negative electrode, a reduced gas containing CO is produced through a $CO_2$ reduction reaction. A catalyst may be used for the negative electrode to promote an electrolytic reaction. The catalyst used for the negative electrode includes a metal such as gold, silver, platinum, palladium, nickel, cobalt, iron, manganese, titanium, cadmium, zinc, indium, and gallium, an alloy containing these metals, a carbon material such as graphene and carbon nanotubes, a metal complex such as a Ru complex, and the like. Furthermore, for example, a catalyst solution containing the metal complex or the like dissolved therein may be brought into contact with the negative electrode.

It is preferable that the electrolyte substance used for the electrolytic device be an aqueous solution containing an arbitrary electrolyte, an ionic liquid, an organic solvent, an organic electrolyte solution, or a solid electrolyte including an ionic conductive membrane or an ionic conductive ceramic. It is preferable that the aqueous solution containing an electrolyte be, for example, an aqueous solution containing at least one of hydroxide ions, hydrogen ions, potassium ions, sodium ions, lithium ions, chloride ions, bromide ions, iodide ions, nitrate ions, sulfate ions, phosphate ion, and the like.

"Methanol Production Method"

Figure 8:
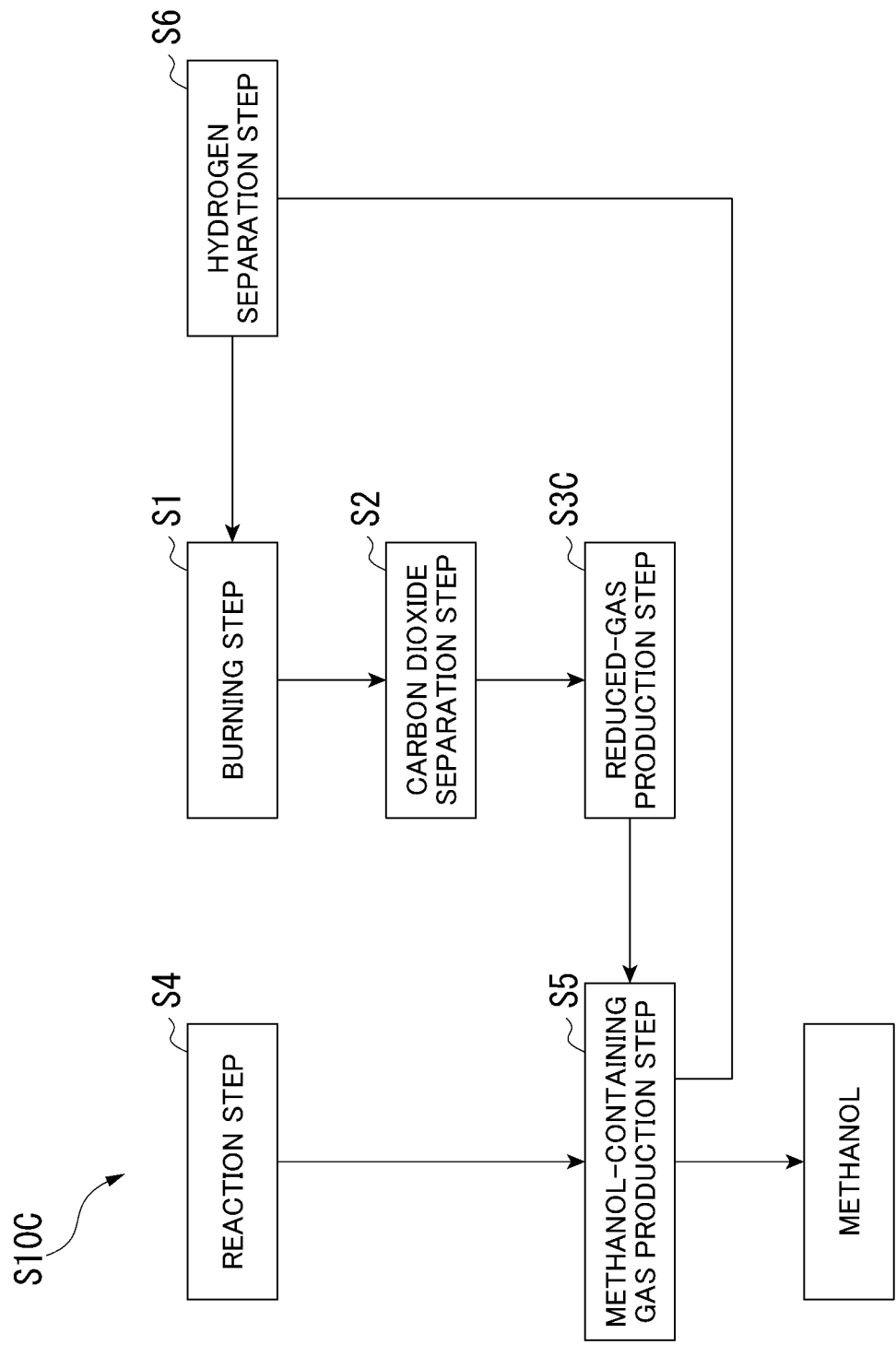
FIG. 8 is a flowchart of a methanol production method according to the fourth embodiment.

A methanol production method in the fourth embodiment will be described below. As shown in FIG. 8, a methanol production method S10C includes a combustion step S1, a carbon dioxide separation step S2, a reduced-gas production step S3C, a reaction step S4, a methanol-containing gas production step S5, and a hydrogen separation step S6. In the following description, constituent elements in the fourth embodiment that are similar to those of the first embodiment, the second embodiment, and the third embodiment are distinguished from those of the first embodiment, the second embodiment, and the third embodiment by attaching different letters after the same reference numerals. Here, among the similar constituent elements, when they have substantially the same functional constitutions as constituent elements which have been described, description of these constituent elements will be omitted. Each step will be described below.

(Reduced-Gas Production Step)

In the reduced-gas production step S3C, $CO_2$ separated out in the carbon dioxide separation step S2 is reduced to produce a reduced gas containing CO. In the case of the reduced-gas generator 4C, CO and $H_2O$ is produced from ethanol and $CO_2$. A specific reaction is represented by the following Expression (12). A reaction at the positive electrode is represented by the following Expression (13) and a reaction at the negative electrode is represented by the following Expression (14):

$$4CO_2 + C_2H_5OH \rightarrow 6CO + 3H_2O \qquad (12)$$

$$C_2H_5OH + 12OH^- \rightarrow 2CO_2 + 9H_2O + 12e^- \qquad (13)$$

$$H_2O + CO_2 + 2e^- \rightarrow CO + 2OH^- \qquad (14).$$

An electrolytic voltage in the foregoing Expression (12) is 0.19 V. Therefore, the methanol production system 10C according to the fourth embodiment can produce a reduced gas at a voltage lower than that of the methanol production system 10 according to the first embodiment. CO generated in this reaction is generated at the negative electrode and $H_2O$ is generated at the positive electrode. The CO generated at the negative electrode is sent to the methanol-containing gas generator 5 through the line L5. The $H_2O$ generated at the positive electrode is discharged through the line L4A as a waste liquid.

(Action and Effect)

In the fourth embodiment described above, when $CO_2$ in the exhaust gas generated through burning is used as a raw material for methanol, it is possible to increase the amount of methanol to be produced while reducing the amount of $CO_2$ releasing into the atmosphere, without increasing the size of the reformer. Furthermore, when ethanol is used in the reduced-gas production step S3C, it is possible to produce a reduced gas with power consumption lower than that in the first embodiment.

Fifth Embodiment

Figure 9:
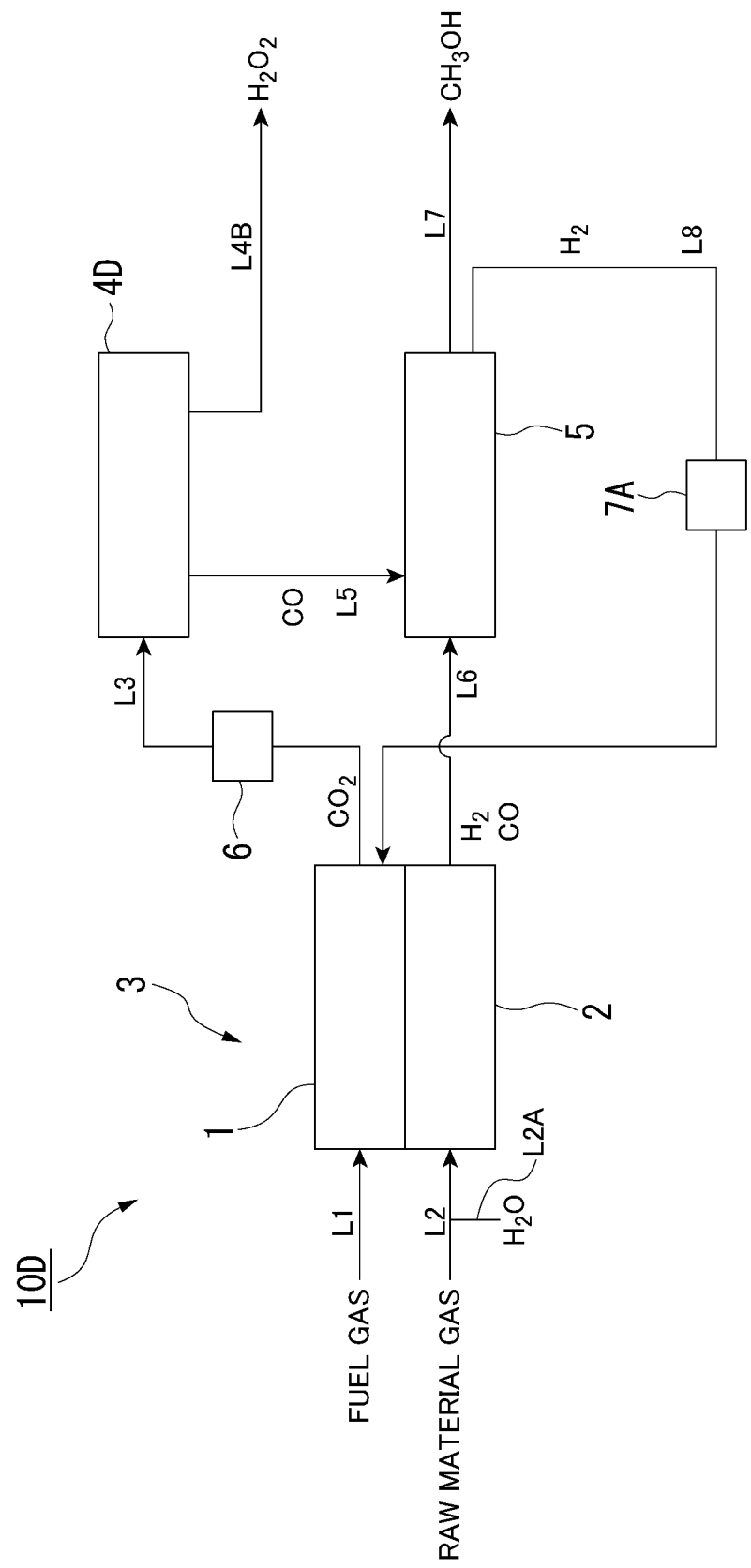
FIG. 9 is a schematic diagram of a methanol production device according to a fifth embodiment.

A fifth embodiment will be described below with reference to FIG. 9. A methanol production system 10D according to the fifth embodiment includes a reformer 3 including a combustion furnace 1 and a reaction furnace 2, a reduced-gas generator 4D, a methanol-containing gas generator 5, a carbon dioxide separator 6, and a hydrogen separator 7A. In the following description, constituent elements in the fifth embodiment that are similar to those of the first embodiment, the second embodiment, the third embodiment, and the fourth embodiment are distinguished from those of the first embodiment, the second embodiment, the third embodiment, and the fourth embodiment by attaching different letters after the same reference numerals. Here, among the similar constituent elements, when they have substantially the same functional constitutions as constituent elements which have been described, a description of these constituent elements will be omitted. Each step will be described below.

(Reduced-Gas Generator)

The reduced-gas generator 4D produces $H_2O_2$ and a reduced gas containing CO from $CO_2$ and $H_2O$ sent through a line L3. The reduced-gas generator 4D in the fifth embodiment is an electrolytic device which includes a positive electrode (not shown), a negative electrode (not shown), and an electrolyte substance (not shown). The reduced-gas generator 4D sends a reduced gas containing CO to the methanol-containing gas generator 5 through a line L5. The reduced-gas generator 4D is connected to the line L3 through which $CO_2$ is introduced into the reduced-gas generator 4D, the line L5 through which the reduced gas produced in the reduced-gas generator 4D is introduced into the methanol-containing gas generator 5, and a line L4B through which $H_2O_2$ is stored respectively.

At the positive electrode, $H_2O_2$ is produced. A catalyst may be used for the positive electrode to promote an electrolytic reaction. A catalyst material used for the positive electrode includes a metal such as platinum, palladium, and nickel, an alloy containing these, a binary metal oxide such as manganese oxide, tungsten oxide, titanium oxide, nickel oxide, cobalt oxide, iron oxide, tin oxide, indium oxide, iridium oxide, and ruthenium oxide, a ternary metal oxide such as Ni—Co—O, Ni—Fe—O, $CaSnO_3$, and $BiVO_4$, a metal complex such as a Ru complex, a diamond electrode, and the like. Furthermore, a catalyst solution containing the metal complex dissolved therein may be brought into contact with the positive electrode.

At the negative electrode, a reduced gas containing CO is produced through a $CO_2$ reduction reaction. A catalyst may be used for the negative electrode to promote an electrolytic reaction. The catalyst used for the negative electrode includes a metal such as gold, silver, platinum, palladium, nickel, cobalt, iron, manganese, titanium, cadmium, zinc, indium, and gallium, an alloy containing these metals, a carbon material such as graphene and carbon nanotubes, a metal complex such as a Ru complex, and the like. Furthermore, for example, a catalyst solution containing the metal complex or the like dissolved therein may be brought into contact with the negative electrode.

It is preferable that the electrolyte substance used in the electrolytic device be an aqueous solution containing an arbitrary electrolyte, an ionic liquid, an organic solvent, an organic electrolyte solution, or a solid electrolyte including an ionic conductive membrane or an ionic conductive ceramic. It is preferable that the aqueous solution containing an electrolyte be, for example, an aqueous solution which contains at least one of hydroxide ions, hydrogen ions, potassium ions, sodium ions, lithium ions, chloride ions, bromide ions, iodide ions, nitrate ions, sulfate ions, phosphate ions, and the like.

"Methanol Production Method"

Figure 10:
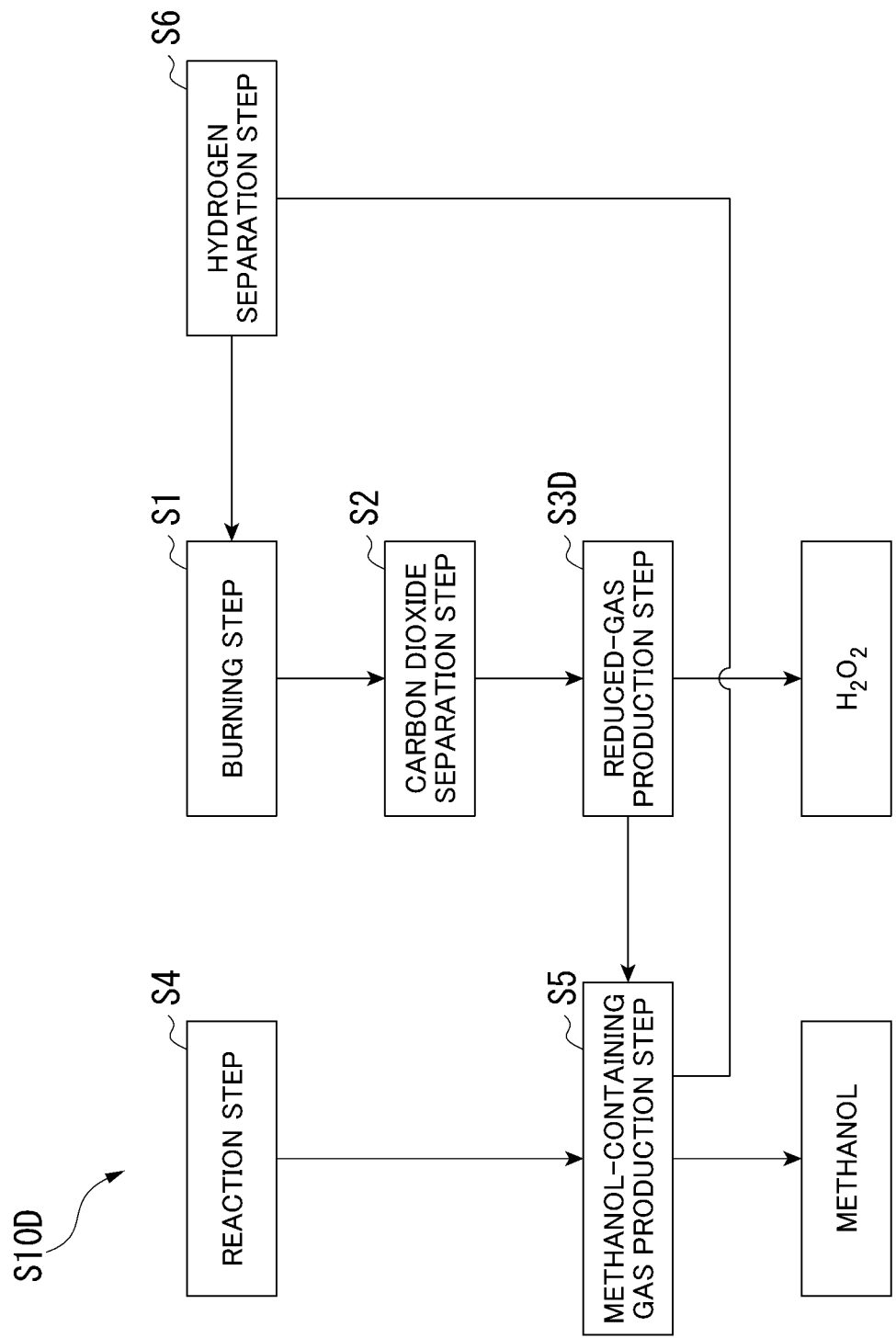
FIG. 10 is a flowchart of a methanol production method according to the fifth embodiment.

A methanol production method in the fifth embodiment will be described below. As shown in FIG. 10, a methanol production method S10D includes a combustion step S1, a carbon dioxide separation step S2, a reduced-gas production step S3D, a reaction step S4, a methanol-containing gas production step S5, and a hydrogen separation step S6. In the following description, constituent elements in the fifth embodiment that are similar to those of the first embodiment, the second embodiment, the third embodiment, and the fourth embodiment are distinguished from those of the first embodiment, the second embodiment, the third embodiment, and the fourth embodiment by attaching different letters after the same reference numerals. Here, among the similar constituent elements, when they have substantially the same functional constitutions as constituent elements which have been described, a description of these constituent elements will be omitted. Each step will be described below.

(Reduced-Gas Production Step)

In the reduced-gas production step S3D, $CO_2$ separated out in the carbon dioxide separation step S2 is reduced to produce a reduced gas containing CO. In the case of the reduced-gas generator 4D, CO and $H_2O_2$ is produced from $H_2O$ and $CO_2$. A specific reaction is represented by the following Expression (15):

$$CO_2 + H_2O \rightarrow CO + H_2O_2 \qquad (15).$$

An electrolytic voltage (vs. SHE) in the foregoing Expression (11) is 1.76 V. In the embodiment, $H_2O_2$ can be produced. CO generated through the reduction reaction is generated at the negative electrode and $H_2O_2$ is generated at the positive electrode. The CO generated at the negative electrode is sent to the methanol-containing gas generator 5 through the line L5. The $H_2O_2$ generated at the positive electrode is stored through the line LAB.

(Action and Effect)

In the fifth embodiment described above, when $CO_2$ in the exhaust gas generated through burning is used for a raw material of methanol, it is possible to increase the amount of methanol to be produced while reducing the amount of $CO_2$ releasing into the atmosphere, without increasing the size of the reformer. Furthermore, it is possible to produce high-value $H_2O_2$.

Sixth Embodiment

Figure 11:
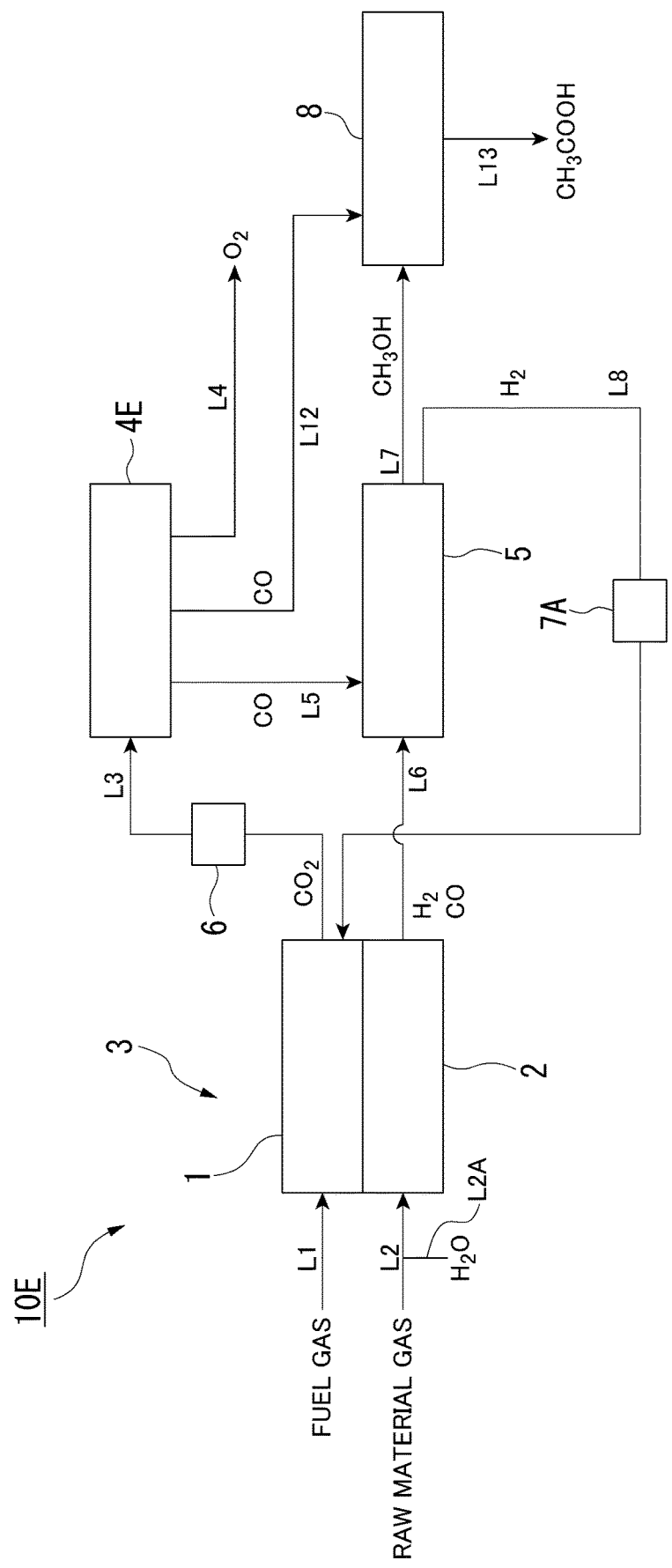
FIG. 11 is a schematic diagram of a methanol production device according to a sixth embodiment.

A sixth embodiment will be described below with reference to FIG. 11. A methanol production system 10E according to the sixth embodiment includes a reformer 3 including a combustion furnace 1 and a reaction furnace 2, a reduced-gas generator 4E, a methanol-containing gas generator 5, a carbon dioxide separator 6, a hydrogen separator 7A, and an acetic acid generator 8. In the following description, constituent elements in the sixth embodiment that are similar to those of the first embodiment, the second embodiment, the third embodiment, the fourth embodiment, and the fifth embodiment are distinguished from those of the first embodiment, the second embodiment, the third embodiment, the fourth embodiment, and the fifth embodiment by attaching different letters after the same reference numerals. Here, among the similar constituent elements, when they have substantially the same functional constitutions as constituent elements which have been described, a description of these constituent elements will be omitted. Each step will be described below.

(Reduced-Gas Generator)

The reduced-gas generator 4E produces a reduced gas containing CO by reducing $CO_2$ sent through a line L3. The reduced-gas generator 4E in the sixth embodiment is an electrolytic device which includes a positive electrode (not shown), a negative electrode (not shown), and an electrolyte substance (not shown). The reduced-gas generator 4E sends a reduced gas containing CO to the methanol-containing gas generator 5 through the line L5. Furthermore, the reduced-gas generator 4E discards $O_2$ through the line L4. The reduced-gas generator 4E is connected to the line L3 through which $CO_2$ is introduced into the reduced-gas generator 4E, the line L5 through which the reduced gas produced in the reduced-gas generator 4E is introduced into the methanol-containing gas generator 5, the line L4 through which the produced $O_2$ is discard, and a line L12 through which a part of the produced CO is introduced into the acetic acid generator 8 respectively.

At the positive electrode, $O_2$ is produced. A catalyst may be used for the positive electrode to promote an electrolytic reaction. A catalyst material used for the positive electrode includes a metal such as platinum, palladium, and nickel, an alloy containing these, a binary metal oxide such as manganese oxide, nickel oxide, cobalt oxide, iron oxide, tin oxide, indium oxide, iridium oxide, and ruthenium oxide, a ternary metal oxide such as Ni—Co—O and Ni—Fe—O, and a metal complex such as a Ru complex. Furthermore, a catalyst solution containing the metal complex or the like dissolved therein may be brought into contact with the positive electrode.

At the negative electrode, a reduced gas containing CO is produced through a $CO_2$ reduction reaction. A catalyst may be used for the negative electrode to promote an electrolytic reaction. The catalyst used for the negative electrode includes a metal such as gold, silver, platinum, palladium, nickel, cobalt, iron, manganese, titanium, cadmium, zinc, indium, and gallium, an alloy containing these metals, a carbon material such as graphene and carbon nanotubes, a metal complex such as a Ru complex, and the like. Furthermore, a catalyst solution dissolving the metal complex or the like dissolved therein may be brought into contact with the negative electrode.

It is preferable that the electrolyte substance used in the electrolytic device be an aqueous solution containing an arbitrary electrolyte, an ionic liquid, an organic solvent, an organic electrolyte solution, or a solid electrolyte including an ionic conductive membrane or an ionic conductive ceramic. It is preferable that the aqueous solution containing an electrolyte be, for example, an aqueous solution which includes at least one of hydroxide ions, hydrogen ions, potassium ions, sodium ions, lithium ions, chloride ions, bromide ions, iodide ions, nitrate ions, sulfate ions, phosphate ions, and the like.

(Acetic Acid Generator)

The acetic acid generator 8 produces acetic acid from methanol in a methanol-containing gas produced in the methanol-containing gas generator 5 and CO sent from the reduced-gas generator 4E. The produced acetic acid is stored through the line L13. Methanol used for producing acetic acid is highly purified in a distillation column (not shown) or the like in the middle of the line L7. The acetic acid generator 8 is connected to the line L7 through which methanol is introduced, the line L12 through which CO produced in the reduced-gas generator 4E is introduced, and the line L13 through which acetic acid produced in the acetic acid generator 8 is stored respectively.

"Methanol Production Method"

Figure 12:
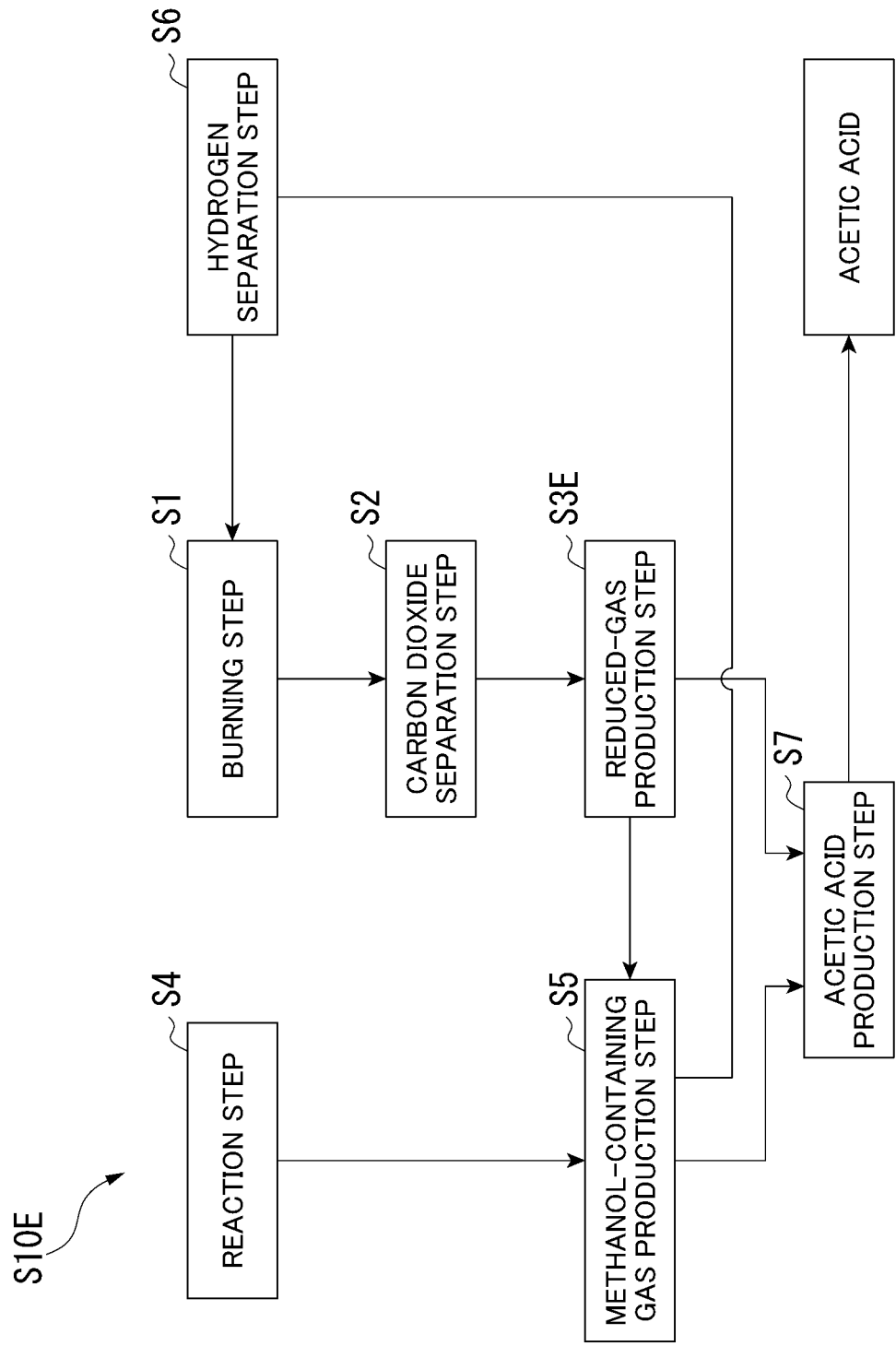
FIG. 12 is a flowchart of a methanol production method according to the sixth embodiment.

A methanol production method in the sixth embodiment will be described below. As shown in FIG. 12, a methanol production method S10E includes a combustion step S1, a carbon dioxide separation step S2, a reduced-gas production step S3E, a reaction step S4, a methanol-containing gas production step S5, a hydrogen separation step S6, and an acetic acid production step S7. In the following description, constituent elements in the sixth embodiment that are similar to those of the first embodiment, the second embodiment, the third embodiment, the fourth embodiment, and the fifth embodiment are distinguished from those of the first embodiment, the second embodiment, the third embodiment, the fourth embodiment, and the fifth embodiment by attaching different letters after the same reference numerals. Here, among the similar constituent elements, when they have substantially the same functional constitutions as constituent elements which have been described, a description of these constituent elements will be omitted. Each step will be described below.

(Reduced-Gas Production Step)

In the reduced-gas production step S3E, $CO_2$ separated out in the carbon dioxide separation step S2 is reduced to produce a reduced gas containing CO. In the case of the reduced-gas generator 4E, a specific reaction is represented by the foregoing Expression (3). CO generated in the reduction reaction is generated at the negative electrode and $O_2$ is generated at the positive electrode. The CO generated in the negative electrode is sent to the methanol-containing gas generator 5 through the line L5. Furthermore, a part of CO is sent to the acetic acid generator 8 through the line L12. $O_2$ generated at the positive electrode is discarded through the line L4.

(Acetic Acid Production Step)

In the acetic acid production step S7, acetic acid is produced from methanol produced in the methanol-containing gas production step S5 and CO produced in the reduced-gas production step S3E. The methanol produced in the methanol-containing gas production step S5 is highly purified through distillation or the like. As a method for producing acetic acid form methanol and CO, a known method can be adopted. For example, the Monsanto process can be used. In the Monsanto process, acetic acid can be produced by causing methanol and CO to react with each other using cobalt iodide as a catalyst and purifying it as appropriate.

(Action and Effect)

In the sixth embodiment described above, when $CO_2$ in the exhaust gas generated through burning is used for a raw material for methanol, it is possible to increase the amount of methanol to be produced while reducing the amount of $CO_2$ releasing into the atmosphere, without increasing the size of the reformer. Furthermore, it is possible to produce high-value acetic acid.

The methanol production system according to each of the embodiments described above may be used independently or in combination with the constitutions described in the embodiments. Furthermore, a known constitution may be applied instead of the constitution described above or a known constitution may be additionally applied to the constitution described in each of the embodiments.

EXAMPLES

Although the present invention will be described in detail with reference to examples, the present invention is not limited thereto.

Example 1

A methanol production system in the first embodiment was prepared. 1500 tons of natural gas which is a raw material gas was reformed using a water vapor reforming method. 200 tons of natural gas which is a fuel gas was used in a combustion reaction for performing reforming. The obtained amount of methanol was 3400 tons. Furthermore, the discharged amount of carbon dioxide was 0 tons.

Example 2

A methanol production system in the sixth embodiment including an acetic acid plant additionally installed therein was prepared. 1500 tons of natural gas which is a raw material gas was reformed. 200 tons of natural gas which is a fuel gas was used in a combustion reaction for performing reforming. The obtained amount of methanol was 1300 tons and an amount of acetic acid was 2400 tons. Furthermore, the discharged amount of carbon dioxide was 0 tons.

Example 3

A methanol production system in the fifth embodiment was prepared. 1500 tons of natural gas which is a raw material gas was reformed. In a combustion reaction for performing reforming, 200 tons of natural gas which is a fuel gas was used. The obtained amount of methanol was 3400 tons. Furthermore, the obtained amount of hydrogen peroxide was 900 tons. The discharged amount of carbon dioxide was 0 tons.

Comparative Example 1

A device obtained by omitting the reduced-gas generator in the methanol production system in the first embodiment was prepared. 1500 tons of natural gas was reformed using a water vapor reforming method. 200 tons of natural gas was used in a combustion reaction for performing reforming. The obtained amount of methanol was 3400 tons. The discharged amount of carbon dioxide which has been calculated was 1000 tons.

From the above, in Example 1 according to the embodiment, it was possible to further reduce an amount of $CO_2$ to be discharged than that in the related art and increase the amount of methanol to be produced.

Supplementary Note

The methanol production system and the methanol production method described in the embodiments described above can be grasped as follows.

(1) A methanol production system 10 according to a first aspect of the present disclosure includes the reformer 3 including the reaction furnace 2 configured to reform methane in a raw material gas to produce a reformed gas containing CO and $H_2$, the reduced-gas generator 4 configured to reduce $CO_2$ to produce a reduced gas containing CO, and the methanol-containing gas generator 5 configured to produce a methanol-containing gas which contains methanol from a reformed gas produced in the reaction furnace 2 and a reduced gas produced in the reduced-gas generator 4.

Thus, it is possible to improve the methanol production capacity and reduce the amount of $CO_2$ to be discharged, without increasing the size of the reformer.

(2) A methanol production system 10 according to a second aspect of the present disclosure is the methanol production system 10 according to (1) and includes the carbon dioxide separator 6 configured to separate out $CO_2$ from exhaust gas.

Thus, it is possible to further reduce an amount of $CO_2$ to be discharged.

(3) A methanol production system 10 according to a third aspect of the present disclosure is the methanol production system 10 according to (2), in which the reformer 3 further includes the combustion furnace 1 configured to supply the heat generated through burning of a fuel gas to the reaction furnace 2 and produce the exhaust gas through burning of the fuel gas.

Thus, it is possible to further reduce the amount of $CO_2$ to be discharged when generated $CO_2$ is used for producing methanol while the heat generated in the combustion furnace is being supplied to the reaction furnace.

(4) A methanol production system 10 according to a fourth aspect of the present disclosure is the methanol production system 10 according to (3) and includes the hydrogen supply path L8 through which $H_2$ is introduced from the methanol-containing gas generator 5 into the combustion furnace 1.

Thus, since it is possible to use the excess $H_2$ left in producing a methanol-containing gas for burning in the combustion furnace, it is possible to further reduce the amount of $CO_2$ to be discharged.

(5) A methanol production system 10 according to a fifth aspect of the present disclosure is the methanol production system 10 according to any one of (1) to (4) and includes the reformed-gas introduction path L9 through which $H_2$ in the reformed gas is introduced from the reaction furnace 2 into the reduced-gas generator 4.

Thus, it is possible to produce CO from $CO_2$ with lower energy.

(6) A methanol production system 10 according to a sixth aspect of the present disclosure is the methanol production system (10) according to any one of (1) to (4) and includes the methanol introduction path through which the methanol-containing gas is introduced from the methanol-containing gas generator into the reduced-gas generator.

Thus, it is possible to produce CO from $CO_2$ with lower energy.

(7) A methanol production system 10 according to a seventh aspect of the present disclosure is the methanol production system 10 according to any one of (1) to (4), in which the reduced-gas generator 4 further uses ethanol.

Thus, it is possible to produce CO from $CO_2$ with lower energy.

(8) A methanol production system 10 according to an eighth aspect of the present disclosure is the methanol production system 10 according to any one of (1) to (4), in which the reduced-gas generator 4 produces CO and $H_2O_2$ from $H_2O$ and the $CO_2$.

Thus, it is possible to produce $H_2O_2$ together with methanol.

(9) A methanol production system 10 according to a ninth aspect of the present disclosure is the methanol production system 10 according to any one of (1) to (4) and includes the acetic acid generator 8 configured to produce acetic acid from methanol in a methanol-containing gas produced in the methanol-containing gas generator 5 and CO in the reduced gas.

Thus, it is possible to produce acetic acid together with methanol

(10) A methanol production system 10 according to a tenth aspect of the present disclosure is the methanol production system 10 according to any one of (1) to (9), in which the reduced-gas generator 4 is an electrolytic device.

Thus, it is possible to efficiently obtain CO from $CO_2$.

(11) A methanol production method S10 according to an eleventh aspect of the present disclosure includes the reaction step S4 of oxidizing methane in a raw material gas to produce a reformed gas containing CO and $H_2$, the reduced-gas production step S3 of reducing $CO_2$ to produce a reduced gas containing CO, and the methanol-containing gas production step S5 of producing a methanol-containing gas which contains methanol from a reformed gas produced in the reaction step S4 and a reduced gas produced in the reduced-gas production step S3.

Thus, it is possible to improve the methanol production capacity and reduce the amount of $CO_2$ to be discharged, without increasing the size of the reformer.

(12) A methanol production method S10 according to a twelfth aspect of the present disclosure is the methanol production method S10 according to (11) and further includes the carbon dioxide separation step S2 of separating out $CO_2$ from exhaust gas.

Thus, it is possible to further reduce an amount of $CO_2$ to be discharged.

(13) A methanol production method S10 according to a thirteenth aspect of the present disclosure is the methanol production method S10 according to (12) and further includes the combustion step S1 of generating the heat used in the reaction step S4 by burning a fuel gas to produce the exhaust gas through burning of the fuel gas.

Thus, it is possible to use the heat generated in the combustion step for the reaction step and further reduce an amount of $CO_2$ to be discharged using $CO_2$ in the generated exhaust gas for a production of methanol.

(14) A methanol production method S10 according to a fourteenth aspect of the present disclosure is the methanol production method S10 according to (13), in which, in the combustion step S1, the excess $H_2$ in producing the methanol-containing gas is further used to perform burning.

Thus, since it is possible to use the excess $H_2$ in producing a methanol-containing gas for performing burning in the combustion furnace, it is possible to further reduce the amount of $CO_2$ to be discharged.

(15) A methanol production method S10 according to a fifteenth aspect of the present disclosure is the methanol production method S10 according to any one of (11) to (14), in which, in the reduced-gas production step S3, a part of $H_2$ in the reformed gas produced in the reaction step S4 is further used.

Thus, it is possible to produce CO from $CO_2$ with lower energy.

(16) A methanol production method S10 according to a sixteenth aspect of the present disclosure is the methanol production method S10 according to any one of (11) to (14), in which, in the reduced-gas production step S3, a part of the methanol-containing gas produced in the methanol-containing gas production step S5 is further used.

Thus, it is possible to produce CO from $CO_2$ with lower energy.

(17) A methanol production method S10 according to a seventeenth aspect of the present disclosure is the methanol production method S10 according to any one of (11) to (14), in which, in the reduced-gas production step S3, ethanol is further used.

Thus, it is possible to produce CO from $CO_2$ with lower energy.

(18) A methanol production method S10 according to an eighteenth aspect of the present disclosure is the methanol production method S10 according to any one of (11) to (14), in which, in the reduced-gas production step S3, CO and $H_2O_2$ are produced from $H_2O$ and the $CO_2$.

Thus, it is possible to produce $H_2O_2$ together with methanol.

(19) A methanol production method S10 according to a nineteenth aspect of the present disclosure is the methanol production method S10 according to any one of (11) to (14) and further includes the acetic acid production step S7 of producing acetic acid from methanol in the methanol-containing gas produced in the methanol-containing gas production step S5 and CO in the reduced gas.

Thus, it is possible to produce acetic acid together with methanol.

(20) A methanol production method S10 according to a twentieth aspect of the present disclosure is the methanol production method S10 according to any one of (11) to (19), in which the reduced-gas production step S3 uses an electrolytic reduction reaction.

Thus, it is possible to efficiently obtain CO from $CO_2$.

The methanol production system and the methanol production method of the present disclosure can improve the methanol production capacity and reduce the amount of $CO_2$ to be discharged, without increasing the size of the reformer, and thus have high industrial applicability.

EXPLANATION OF REFERENCES

1 Combustion furnace
2 Reaction furnace
3 Reformer
4 Reduced-gas generator
5 Methanol-containing gas generator
6 Carbon dioxide separator
7A Hydrogen separator
10 Methanol production system
L1, L2, L3, L4, L5, L6, L7 Line

What is claimed is:
1. A methanol production system, comprising:
a reformer including a reaction furnace configured to reform methane in a raw material gas to produce a reformed gas containing CO and Hz;
a reduced-gas generator configured to reduce CO2 to produce a reduced gas containing CO;
a methanol-containing gas generator configured to produce a methanol-containing gas which contains methanol from a reformed gas produced in the reaction furnace and the reduced gas produced in the reduced-gas generator; and
a carbon dioxide separator configured to separate out the CO2 from exhaust gas,
wherein the reformer further includes a combustion furnace configured to supply heat generated through burning of a fuel gas to the reaction furnace and to produce the exhaust gas through burning of the fuel gas, and
the methanol production system further comprises a hydrogen supply path through which $H_2$ is introduced from the methanol-containing gas generator into the combustion furnace.

2. The methanol production system according to claim 1, comprising:
a reformed-gas introduction path through which $H_2$ in the reformed gas is introduced from the reaction furnace into the reduced-gas generator.

3. The methanol production system according to claim 1, comprising:
a methanol introduction path through which the methanol-containing gas is introduced from the methanol-containing gas generator into the reduced-gas generator.

4. The methanol production system according to claim 1, wherein the reduced-gas generator further uses ethanol.

5. The methanol production system according to claim 1, wherein the reduced-gas generator produces CO and $H_2O_2$ from $H_2O$ and the $CO_2$.

6. The methanol production system according to claim 1, comprising:
an acetic acid generator configured to produce acetic acid from methanol in a methanol-containing gas produced in the methanol-containing gas generator and CO in the reduced gas.

7. The methanol production system according to claim 1, wherein the reduced-gas generator is an electrolytic device.

8. A methanol production method using the methanol production system according to claim 1, comprising:
a reaction step of oxidizing methane in a raw material gas to produce a reformed gas containing CO and $H_2$;
a reduced-gas production step of reducing $CO_2$ to produce a reduced gas containing CO; and
a methanol-containing gas production step of producing a methanol-containing gas which contains methanol from a reformed gas produced in the reaction step and the reduced gas produced in the reduced-gas production step,
a carbon dioxide separation step of separating out the $CO_2$ from exhaust gas, and
a combustion step of generating heat used in the reaction step by burning a fuel gas to produce the exhaust gas through burning of the fuel gas,
wherein, in the combustion step, the excess $H_2$ in producing the methanol-containing gas is further used to perform burning.

9. The methanol production method according to claim 8, wherein, in the reduced-gas production step, a part of $H_2$ in the reformed gas produced in the reaction step is further used.

10. The methanol production method according to claim 8, wherein, in the reduced-gas production step, a part of the methanol-containing gas produced in the methanol-containing gas production step is further used.

11. The methanol production method according to claim 8, wherein, in the reduced-gas production step, ethanol is further used.

12. The methanol production method according to claim 8, wherein, in the reduced-gas production step, CO and $H_2O_2$ are produced from $H_2O$ and the $CO_2$.

13. The methanol production method according to claim 8, further comprising:
an acetic acid production step of producing acetic acid from methanol in the methanol-containing gas produced in the methanol-containing gas production step and CO in the reduced gas.

14. The methanol production method according to claim 8, wherein the reduced-gas production step uses an electrolytic reduction reaction.

* * * * *